(12) United States Patent
Danks et al.

(10) Patent No.: US 6,800,483 B1
(45) Date of Patent: Oct. 5, 2004

(54) COMPOSITIONS AND METHODS FOR SENSITIZING AND INHIBITING GROWTH OF HUMAN TUMOR CELLS

(75) Inventors: Mary K. Danks, Memphis, TN (US); Philip M. Potter, Memphis, TN (US); Peter J. Houghton, Memphis, TN (US)

(73) Assignee: St. Jude Childrens Research Hospital, Memphis, TN (US)

( * ) Notice: Subject to any disclaimer, the term of this patent is extended or adjusted under 35 U.S.C. 154(b) by 0 days.

(21) Appl. No.: 09/595,682

(22) Filed: Jun. 16, 2000

Related U.S. Application Data

(63) Continuation-in-part of application No. PCT/US99/03171, filed on Feb. 12, 1999.
(60) Provisional application No. 60/075,258, filed on Feb. 19, 1998.

(51) Int. Cl.$^7$ .................. C12N 15/09; C12N 15/63; C12N 15/85
(52) U.S. Cl. ............. 435/456; 435/320.1; 435/325
(58) Field of Search ................ 435/320.1, 325, 435/456; 514/44; 800/8

(56) References Cited

U.S. PATENT DOCUMENTS 6,107,549 A  8/2000  Feng et al. .............. 800/300

OTHER PUBLICATIONS

Anderson, Human gene therapy, 1998, NATURE, vol. 392, pp. 25–30.*
Walther et al., Viral vectors for gene transfer, 2000, DRUGS, vol. 60, pp. 249–271.*
Rigg et al., genetic prodrug activation therapy, 1997, Molecular Medicine, pp. 359–366.*
Mountain, Gene therapy: the first decade, 2000, TIBTECH, vol. 18, pp. 119–125.*
Crystal, Transfer of genes to humans: Early lessons and obstacles to success, 1995, SCIENCE, vol. 270, pp. 404–409.*
Verma et al., Gene therapy–promises, problems and prospects, 1997, NATURE, vol. 389, pp. 239–241.*
Riddles, et al., "Cloning and analysis of a cDNA encoding a human liver carboxylesterase", Gene 1991 108:289–292.
Ozols et al., "Isolation, Properties and the Complete Amino Acid Sequence of a Second Form of 60–kDa Glycoprotein Esterase", J. Biol. Chem. 1989 264(21):12533–12545.
Niculescu–Duvaz et al., "Gene–Directed Enzyme Prodrug Therapy", Bioconjugate Chem. 1998 9:4–22.
Niculescu–Duvaz et al., "Antibody–directed enzyme prodrug therapy (ADEPT):a review", Advanced Drug Delivery Reviews 1997 26:151–172.
Pawlik et al., "Use of the Ornithine Decarboxylase Promoter to Achieve N–MYC–Mediated Overexpression of a Rabbit Carboxylesterase to Sensitize Neuroblastoma Cells to CPT–11", Molecular Therapy 2000 1(5):457–463.

Meck et al., "A Virus–directed Enzyme Prodrug Therapy Approach to Purging Neuroblastoma Cells from hematopoietic Cells Using Adenovirus Encoding Rabbit Carboxylesterase and CPT–11[1]", Cancer Research 2001 61:5083–5089.
Guichard et al., "Conversion of the CPT–11 Metabolite APC to SN–38 by Rabbit Liver Carboxylesterase[1]", Clinical Cancer Research 1998 4:3089–3094.
Wadkins et al., "Structural Constraints Affect the metabolism of 7–Ethyl–10–[4–(1–piperidino)–1–piperidino]carbonyloxycamptothecin (CPT–11) by Carboxylesterases", Mol. Pharmocol. 2001 60(2):355–362.
Bello–Fernandez, C., et al., "The ornithine decarboxylase gene is a transcriptional target of c–Myc", 1993 Proc. Natl. Acad. Sci. USA 90:7804–7808.
Brodeur, G.M., et al., "Biology and Genetics of Human Neuroblastomas", 1997 J. Ped. Hematol. Oncol. 19:93–101.
Dachs et al., "Targeting Gene Therapy to Cancer: A Review", 1997 Oncol. Res. 9:313–325.
Davis et al., "Current progress in the gene therapy of cancer", 1996 Current Opinion in Oncology 8:499–508.
Field, et al., "Elevated expression of the c–myc oncoprotein correlates with poor prognosis in head and neck squamous cell carcinoma", 1989 Oncogene 4:1463–1468.
Haaz, M.C., et al., "Metabolism of Irinotecan (CPT–11) by Human Hepatic Microsomes: Participation of Cytochrome P–450 3A and Drug Interactions[1]", 1998 Cancer Res. 58:468–472.
Hanania et al., "Recent Advances in the Application of Gene Therapy to Human Disease", 1995 Am. Jour. Med. 99:537–552.
Houghton, P.J., et al., "Efficacy of topoisomerase 1 inhibitors, topotecan and irinotecan, adminstered at low dose levels in protracted schedules to mice bearing xenografts of human tumors", 1995 36:393–403.
Houghton, P.J., et al., "Therapeutic Efficacy of the Topoisomerase I Inhibitor 7–Ethyl–10–(4–[1–piperidino]–1–piperidino)–carbonyloxy–camptothecin against Human Tumor Xenografts:Lack of Cross–Resistance in Vivo in Tumors with Acquired Resistance to the Topoisomerase I Inhibitor 9–Dimethylaminomethyl–10–hydroxycamptothecin[1]", 1993 53:2823–2829.
Hsiang, Y.–H. et al., "Arrest of Replication Forks by Drug–stabilized Topoisomerase I–DNA Cleavable Complexes as a Mechanism of Cell Killing by Camptothecin[1]", 1989 Cancer Res. 49:5077–5082.

(List continued on next page.)

Primary Examiner—Anne-Marie Falk
Assistant Examiner—Celine Qian
(74) Attorney, Agent, or Firm—Licata & Tyrrell P.C.

(57) ABSTRACT

Polynucleotides encoding carboxylesterase enzymes and polypeptides encoded by the polynucleotides which are capable of metabolizing a chemotherapeutic prodrug and inactive metabolites thereof to active drug are provided. Compositions and methods for sensitizing tumor cells to a prodrug chemotherapeutic agent and inhibiting tumor growth with this enzyme are also provided. In addition, screening assay for identification of drugs activated by this enzyme are described.

4 Claims, 14 Drawing Sheets

OTHER PUBLICATIONS

Humerickhouse et al., "Characterization of CPT–11 Hydrolysis by Human Liver Carboxylesterase Isoforms hCE–1 and hCE–2[1]", 2000 *Cancer Res.* 60:1189–1192.

Johnson et al., "Current therapy for cutaneous melanoma", 1995 *J. Am. Acad. Derm.* 32(5):689–707.

Kaneda, N. et al., "Metabolism and Pharmacokinetics of the Camptothecin Analogue CPT–11 in the Mouse", 1990 *Cancer Res.* 50:1715–1720.

Kawasaki, H. et al., "Specific Regulation of Gene Expression by Antisense Nucleic Acids: A Summary of Methodologies and Associated Problems", 1996 *Artif. Organs* 20(8):836–848.

Kawato, Y. et al., "Intracellular Roles of SN–38, a Metabolite of the Camptothecin Derivative CPT–11, in the Antitumor Effect of CPT–11", 1991 *Cancer Res.* 51:4187–4191.

Korza, G. and J. Ozols, "Complete Covalent Structure of 60–kDa Esterase Isolated from 2,3,7,8–Tetrachlorodibenzo–p–dioxin–induced Rabbit Liver Microsomes" 1988 *J. Biol. Chem.* 263:3486–3495.

Kumagai, T. et al., "Eradication of Myc–overexpressing Small Cell Lung Cancer Cells Transfected with Herpes Simplex Virus Thymidine Kinase Gene Containing Myc-Max Response Elements[1]", 1996 *Cancer Res.* 56(2):354–358.

Leinweber, F.J., "Possible Physiological Roles of Carboxylic Ester Hydrolases", 1987 *Drug Metab. Rev.* 18:379–439.

Lutz et al., "Conditional expression of N–*myc* in human neuroblastoma cells increases expression of α–prothymosin and ornithine decarboxylase and accelerates progression into S–phase early after mitogenic stimulation of quiescent cells", 1996 *Oncogene* 13:803–812.

Matthay, K.E., "Neuroblastoma:Biology and Therapy", 1997 *Oncology* 11:1857–1875.

Matthay, K.E., et al., "Patterns of Relapse After Autologous Purged Bone Marrow Transplantation for Neuroblastoma: A Childrens Cancer Group Pilot Study", 1993 *J. Clin. Oncol.* 11:2226–2233.

Nagai, M.A., et al., "Association of Genetic Alterations of c–*myc*, c–*fos*, and c–Ha–*ras* Proto–Oncogenes in Colorectal Tumors", 1992 *Dis. Colon Rectum* 35:444–451.

Orian, J.M., et al., "Overexperssion of multiple oncogenes related to histological grade of astrocytic glioma", 1992 *Br. J. Cancer* 66:106–112.

Raschella, G., et al., "Lack of Correlation between N–*myc* and MAX Expression in Neuroblastoma Tumors and in Cell Lines: Implication for N–*myc*–MAX Complex Formation[1]", 1994 *Cancer Res.* 54:2251–2255.

Rill, D.R., et al., "Direct Demonstration That Autologous Bone Marrow Transplantation for Solid Tumors Can Return a Multiplicity of Tumorigenic Cells", 1994 *Blood* 84:380–383.

Riou, G., et al., "C–*myc* Proto–Oncogene Expression and Prognosis in Early Carcinoma of the Uterine Cervix", 1987 *Lancet* 2:761–763.

Rivory, et al., "Identification and Properties of a Major Plasma Metabolite of Irinotecan (CPT–11) Isolated from the Plasma of Patients[1]", 1996 *Cancer Res.* 56:3689–3694.

Rivory, L.P., et al., "Pharmacokinetic Interrelationships of Irinotecan (CPT–11) and Its Three Major Plasma Metabolites in Patients Enrolled in Phase I/II Trials[1]", 1997 *Clin. Cancer Res.* 56:3689–3694.

Roth and Cristiano, "Gene Therapy for Cancer: What Have We Done and Where Are We Going?", 1997 *J. Natl. Canc. Inst.* 89(1):21–39.

Rowinsky, E.K., et al., "Phase I and Pharmacological Study of the Novel Topoisomerase I Inhibitor 7–Ethyl–10–[4–(1–piperidino)–1–piperidno]carbonyloxycamptothecin (CPT–11) Administred as a Ninety–Minute Infusion Every 3 Weeks[1]", 1994 *Cancer Res.* 54:427–436.

Satoh, T., et al., "Metabolic Activation of CPT–11, 7–Ethyl–10–[4–1(piperidino)–1–piperidino]carbonyloxy-camptothecin, a Novel Antitumor Agent, by Carboxylesterase" 1994 *Biol. Pharm. Bull.* 17:662–664.

Senter, P.D., et al., "The Role of Rat Serum Carboxylesterase in the Activation of Paclitaxel and Camptothecin Prodrugs", 1996 *Cancer Res.* 56:1471–1474.

Tanizawa, A., et al., "Comparison of Topoisomerase I Inhibition, DNA Damage, and Cytotoxicity of Camptothecin Derivatives Presently in Clinical Trials", 1994 *J. Natl. Cancer Inst.* 86:836–842.

Tsuji, T., et al., "CPT–11 Converting Enzyme from Rat Serum:Purification and Some Properties", 1991 *J. Pharmacobio. Dynamics* 14:341–349.

Yamada, H., et al., "Amplifications of Both c–Ki–*ras* with a Point Mutation and c–*myc* in a Primary Pancreatic Cancer and its Metastatic Tumors in Lymph Nodes", 1986 *Jpn. J. Cancer Res.* 77:370–375.

Yang, N.S., "Gene Transfer into Mammalian Somatic Cells In Vivo", 1992 *Crit. Rev. Biotechnol.* 12:335–356.

* cited by examiner

```
Residue#
Rabbit AA                                                       HPSAPVXVDTVHGKVLGKFVSXEGEAQPVAKEXG
                                                                |||||  ||||| ||||||||||  ||| ||||
Rabbit    (P12337)                                              HPSAPPVVDTVRGKVLGKFVSLEGFAQPVAVFLGVP
Human     (P23141)   MWLRAFILATLSASAAWGHPSSSPPVVDTVHGKVLGKFVSLEGFAQPVAIFLGIP
Rat       (P10959)   MWLCALVWASLAVCPIWGHPSSSPPVVDTTKGKVLGKYVSLEGFTQPVAVFLGVP
Mouse     (P23953)   MWLHALVWASLAVCPILGHSLLPPVVDTTQGKVLGKYISLEGFEQPVAVFLGVP
```

FIGURE 1

```
Residue #                1                      5      Residue #                                    518
Amino acid sequence      His Pro Ser Ala Pro           Amino acid sequence  Ala Phe Trp Thr Glu Leu Trp
Coding Sequence          CAC CCA AGC GCA CC            Coding sequence      GCA TTC TGG ACA GAA CTA TGG
                         T   G   T   G                                          G   T   G   G   A   G
                             C       C                                          C       C   C       C
                             T                                                  T       T   T       T Oligonucleotide          CAC CCI AGC GCI CC            Reverse complement   CCA AAG TTC AGT CCA GAA AGC
Rab51                        T       T                                          G   C   G   G   A   G
                                                                                C   T   C   C       C
                                                                                T       T   T       T Amino acid sequence      His Pro Ser Ala Pro           Oligonuclsotide      CCA IAG TTC IGT VVA GAA IGC
Coding Sequence          CAC CCA AGC GCA CC            Rab 31                   C                   A
                         T   G   T   G
                             C       C
                             T Oligonucleotide          CAC CCI TCI GCI CC            Amino acid sequence  Ala Phe Trp Thr Glu Leu Trp
Rab 52                                                 Coding sequence      GCA TTC TGG ACA GAA CTA TGG
                                                                                G   T   G   G   A   G
                                                                                C       C   C       C
                                                                                T       T   T       T Reverse compliment   CCA TAA TTC AGT CCA GAA AGT
                                                                                C   C   G   G   A   G
                                                                                        C   C       C
                                                                                T       T   T       T Oligonucleotide      CCA TAA TTC IGT CCA GAA IGC
                                                       Rab 52                   C   C               A
```

FIGURE 2

| Residue # | | |
|---|---|---|
| Rabbit | | MWLCALALASLAACTAWGHPSAPPVVDTVK |
| Rat | (P10959) | MWLCALVWASLAVCPIWGHPSSPPVVDTTK |
| Human | (P23141) | MWLRAFILATLSASAAWGHPSSPPVVDTVH |
| Rat | (P16303) | MRLYPLVWLFLAACTAWGYPSSPPVVNTVK |
| Mouse | (P23953) | MWLHALVWASLAVCPILGHSLLPPVVDTTQ |

FIGURE 3

```
GAATTCTGCC ATG TGG CTC TGT GCA TTG GCC CTG GCC CTG GCC TCT CTC GCC GCT TGC ACG GCT TGG GGG CAC CCG TCT GCA CCA
              Met Trp Leu Cys Ala Leu Ala Leu Ala Ser Leu Ala Ala Cys Thr Ala Trp Gly His Pro Ser Ala Pro
   1                                                     50                                          150

CCT GTG GTA GAT ACT GTG CAT GGC AAA GTC CTG GGG AAG TTC GTC AGC TTA GAA GGA TTT GCA CAG CCC GTG GCC
24  Pro Val Val Asp Thr Val His Gly Lys Val Leu Gly Lys Phe Val Ser Leu Glu Gly Phe Ala Gln Pro Val Ala
                              100

GTC TTC CTG GGA GTC CCC AAG CCC CCT CTT GGA TCC AGG TTT GCA CCA CAG CCT GCA GAA TCA
49  Val Phe Leu Gly Val Pro Lys Pro Pro Leu Gly Ser Arg Phe Ala Pro Gln Pro Ala Glu Ser
                                                       200

TTG AGC CAC GTG AAG AAC ACC TCC CCT TAC CCT CCC ATG TGC CAG GAC GTA TCA GGG CAT ATG CTC TCG
74  Leu Ser His Val Lys Asn Thr Ser Pro Tyr Pro Pro Met Cys Gln Asp Val Ser Gly His Met Leu Ser
                     250                                                        300

GAG CTC TTC ACC AAC AGA AAA GAG AAC ATC CCT CTT AAG TTT TCT GAA GAC TGC CTT TAC CTG AAT ATT TAC ACC
99  Glu Leu Phe Thr Asn Arg Lys Glu Asn Ile Pro Leu Lys Phe Ser Glu Asp Cys Leu Tyr Leu Asn Ile Tyr Thr
                                                                              350

CCT GCT GAC CTG ACA AAG AGA GGC AGG CTG ATG CCG GTG ATG GGT GGT CTG ATG GTG GGT GGA
124 Pro Ala Asp Leu Thr Lys Arg Gly Arg Leu Met Pro Val Met Trp Ile His Gly Gly Leu Met Val Gly Gly
                   400                                                 450

GCA TCA ACC TAT GAT GGC CTG GCT CTT TCT GCC CAT GAG AAC GTG GTG GTG ACC ATT CAG TAC CGC CTG GGC
149 Ala Ser Thr Tyr Asp Gly Leu Ala Leu Ser Ala His Glu Asn Val Val Val Thr Ile Gln Tyr Arg Leu Gly
                                                          500

ATC TGG GGA TTC TTC AGC ACA GGA GAT GAG CAC AGC CGA GGG AAC TGG GGT CAC TTG GAC CAG GTG GCT GCG CTG
174 Ile Trp Gly Phe Phe Ser Thr Gly Asp Glu His Ser Arg Gly Asn Trp Gly His Leu Asp Gln Val Ala Ala Leu
                    550                                                        600

CGG TGG GTC CAG GAC AAC ATT GCC AAC TTT GGA GGG GAC CCA GGC TCT GTG ACC ATC TTT GGA GAG TCA GCA GGA
199 Arg Trp Val Gln Asp Asn Ile Ala Asn Phe Gly Gly Asp Pro Gly Ser Val Thr Ile Phe Gly Glu Ser Ala Gly
                                                 650

FIGURE 4
```

```
TAT CGG TAT CGC CCA AGC TTC TCA TCA GAC ATG AGA CCC AAG ACA GTG ATA GGG GAC CAT GGA GAT GAG ATC TTC
Glu Tyr Arg Tyr Arg Pro Ser Phe Ser Ser Asp Met Arg Pro Lys Thr Val Ile Gly Asp His Gly Asp Glu Ile

TCT GTC TTA GGA GCC CCG TTT TTA AAA GAG GGT GCC ACA GAA GAG ATC AAA CTG AGC AAG ATG GTG ATG AAA
Phe Ser Val Leu Gly Ala Pro Phe Leu Lys Glu Gly Ala Thr Glu Glu Ile Lys Leu Ser Lys Met Val Met

TAC TGG GCC AAC TTT GCT AGG AAT GGA AAT CCC AAT GGA GAA GGG CTT CCT CAA TGG CCA GCA TAT GAC TAC AAG
Lys Tyr Trp Ala Asn Phe Ala Arg Asn Gly Asn Pro Asn Gly Glu Gly Leu Pro Gln Trp Pro Ala Tyr Asp Tyr

GAA GGT TAC CTG CAG ATT GGA GCC ACC CAG GCA GCC CAG AAA CTG AAA GAC AAG GAA GTG GCT TTC TGG ACT
Lys Gly Tyr Leu Gln Ile Gly Ala Thr Gln Ala Ala Gln Lys Leu Lys Asp Lys Glu Val Ala Phe Trp

GAG CTC TGG GCC AAG GAG GCA GCA AGG CCA CGT GAG ACA GAG CAC ATT GAG CTG TGA ATT GAATTC
Thr Glu Leu Trp Ala Lys Glu Ala Ala Arg Pro Arg Glu Thr Glu His Ile Glu Leu
```

FIGURE 4 CONTINUED

```
GGA GGT CAA AGT GTC TCT ATC CTT CTA TTA TCC CCC CTG ACC AAG AAT CTC TTC CAT CGA GCA ATT TCC GAG AGT
Ala Gly Gln Ser Val Ser Ile Leu Leu Leu Ser Pro Leu Thr Lys Asn Leu Phe His Arg Ala Ile Ser Glu

GGC GTG GCC CTC CTT TCC AGT CTC TTC AGG AAG AAC ACC AAG TCC TTG GCT GAG AAA ATT GCC ATC GAA GCT GGG
Ser Gly Val Ala Leu Leu Ser Ser Leu Phe Arg Lys Asn Thr Lys Ser Leu Ala Glu Lys Ile Ala Ile Glu Ala

TGT AAA ACC ACC ACC TCG GCT GTC ATG GTT CAC TGC CTG CGC CAG AAG ACA GAG GAA CTC ATG GAG GTG ACA
Gly Cys Lys Thr Thr Thr Ser Ala Val Met Val His Cys Leu Arg Gln Lys Thr Glu Glu Leu Met Glu Val

TTG AAA ATG AAA TTT ATG GCT CTA GAT CTA GGT CCC ARA GAG AAC GCC TTC CTG ACC ACT GTG ATT
Thr Lys Met Lys Phe Met Ala Leu Asp Leu Gly Val Asp Pro Lys Glu Asn Ala Phe Leu Thr Thr Val

GAT GGG GTG CTG CCA AAA CCT GCA GAG ATT CTG GCA GAG AAA TAC AAC ATG CCC TAC ATG GTG
Ile Asp Gly Val Leu Pro Lys Leu Ala Glu Ile Leu Ala Glu Lys Tyr Asn Met Pro Tyr Met

GGA ATC AAC CAG GAG TTT GGC TGG ATT CAA ATG CTG GGC TAT CCA CTC GAA CTC TCT AAG GGC AAA CTG
Val Gly Ile Asn Gln Glu Phe Gly Trp Ile Gln Met Leu Gly Tyr Pro Leu Glu Ser Glu Gly Lys

GAC CAG AAC ACA GCT ACA GAA CTC TTG TGG AAG TCC TAC CCC ATT GTC AAT GTC TCT AAG GAG CTG ACT CCA GTG
Leu Asp Gln Asn Thr Ala Thr Glu Leu Leu Trp Lys Ser Tyr Pro Ile Val Asn Val Ser Lys Glu Leu Thr Pro

GCC ACT GAG AAG TAT TTA GGA GGG ACA GAT GAC CCT GTC ARA AAG GAT GCT CGT CTT CTG TTC CTG GAC ATG GCA GAT
Val Ala Thr Glu Lys Tyr Leu Gly Gly Thr Asp Asp Pro Val Lys Lys Asp Ala Arg Leu Leu Phe Leu Asp Met Ala

TTG TTA TTT GGT GTC CCA TCT GTG AAT GTG GCT CGT GCT CAC AGA GAT GCT CGT GCC CCC ACC TAT ATG TAT GAG
Asp Leu Leu Phe Gly Val Pro Ser Val Asn Val Ala Arg His Arg Asp Ala Pro Thr Tyr Met Tyr
```

FIGURE 4 CONTINUED

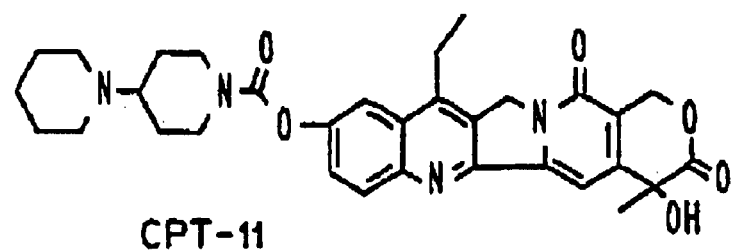
CPT-11
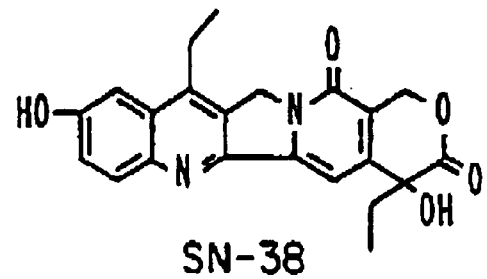
SN-38
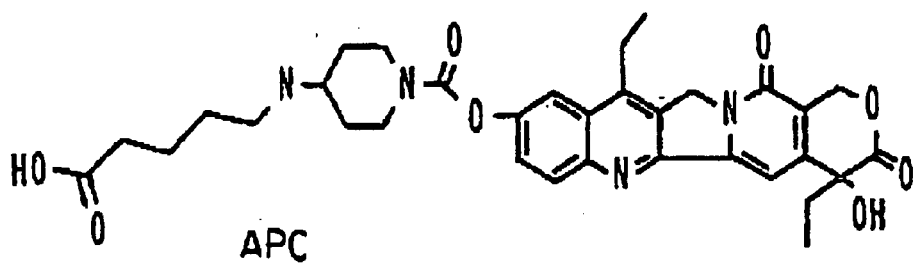
APC
*Fig. 8*

SEQUENCE LISTING

```
<160> NUMBER OF SEQ ID NOS: 30

<210> SEQ ID NO 1
<211> LENGTH: 34
<212> TYPE: PRT
<213> ORGANISM: Artificial Sequence
<220> FEATURE:
<221> NAME/KEY: UNSURE
<222> LOCATION: (7)
<221> NAME/KEY: UNSURE
<222> LOCATION: (33)
<221> NAME/KEY: UNSURE
<222> LOCATION: (22)
<223> OTHER INFORMATION: Synthetic

<400> SEQUENCE: 1

His Pro Ser Ala Pro Val Xaa Val Asp Thr Val His Gly Lys Val Leu
  1               5                  10                  15

Gly Lys Phe Val Ser Xaa Glu Gly Phe Ala Gln Pro Val Ala Lys Phe
             20                  25                  30

Xaa Gly

<210> SEQ ID NO 2
<211> LENGTH: 36
<212> TYPE: PRT
<213> ORGANISM: Oryctolagus cuniculus

<400> SEQUENCE: 2

His Pro Ser Ala Pro Pro Val Val Asp Thr Val Lys Gly Lys Val Leu
  1               5                  10                  15

Gly Lys Phe Val Ser Leu Glu Gly Phe Ala Gln Pro Val Ala Val Phe
             20                  25                  30

Leu Gly Val Pro
         35

<210> SEQ ID NO 3
<211> LENGTH: 54
<212> TYPE: PRT
<213> ORGANISM: Homo sapiens

<400> SEQUENCE: 3

Met Trp Leu Arg Ala Phe Ile Leu Ala Thr Leu Ser Ala Ser Ala Ala
```

```
              1               5              10              15

Trp Gly His Pro Ser Ser Pro Val Val Asp Thr Val His Gly Lys
             20                  25                  30

Val Leu Gly Lys Phe Val Ser Leu Glu Gly Phe Ala Gln Pro Val Ala
         35                  40                  45

Ile Phe Leu Gly Ile Pro
        50

<210> SEQ ID NO 4
<211> LENGTH: 54
<212> TYPE: PRT
<213> ORGANISM: Rattus sp.

<400> SEQUENCE: 4

Met Trp Leu Cys Ala Leu Val Trp Ala Ser Leu Ala Val Cys Pro Ile
 1               5                  10                  15

Trp Gly His Pro Ser Ser Pro Val Val Asp Thr Thr Lys Gly Lys
             20                  25                  30

Val Leu Gly Lys Tyr Val Ser Leu Glu Gly Phe Thr Gln Pro Val Ala
         35                  40                  45

Val Phe Leu Gly Val Pro
        50

<210> SEQ ID NO 5
<211> LENGTH: 54
<212> TYPE: PRT
<213> ORGANISM: Mus musculus

<400> SEQUENCE: 5

Met Trp Leu His Ala Leu Val Trp Ala Ser Leu Ala Val Cys Pro Ile
 1               5                  10                  15

Leu Gly His Ser Leu Leu Pro Pro Val Val Asp Thr Thr Gln Gly Lys
             20                  25                  30

Val Leu Gly Lys Tyr Ile Ser Leu Glu Gly Phe Glu Gln Pro Val Ala
         35                  40                  45

Val Phe Leu Gly Val Pro
        50

<210> SEQ ID NO 6
<211> LENGTH: 5
<212> TYPE: PRT
<213> ORGANISM: Oryctolagus cuniculus

<400> SEQUENCE: 6

His Pro Ser Ala Pro
 1               5

<210> SEQ ID NO 7
<211> LENGTH: 14
<212> TYPE: DNA
<213> ORGANISM: Oryctolagus cuniculus

<400> SEQUENCE: 7
cacccaagcg cacc                                                      14

<210> SEQ ID NO 8
<211> LENGTH: 14
<212> TYPE: DNA
<213> ORGANISM: Artificial Sequence
<220> FEATURE:
<223> OTHER INFORMATION: Description of Artificial Sequence: Synthetic
```

```
<221> NAME/KEY: unsure
<222> LOCATION: (6)
<221> NAME/KEY: unsure
<222> LOCATION: (12)

<400> SEQUENCE: 8
cacccnagcg cncc                                                              14

<210> SEQ ID NO 9
<211> LENGTH: 14
<212> TYPE: DNA
<213> ORGANISM: Artificial Sequence
<220> FEATURE:
<223> OTHER INFORMATION: Description of Artificial Sequence: Synthetic
<221> NAME/KEY: unsure
<222> LOCATION: (6)
<221> NAME/KEY: unsure
<222> LOCATION: (9)
<221> NAME/KEY: unsure
<222> LOCATION: (12)

<400> SEQUENCE: 9
cacccntcng cncc                                                              14

<210> SEQ ID NO 10
<211> LENGTH: 7
<212> TYPE: PRT
<213> ORGANISM: Oryctolagus cuniculus

<400> SEQUENCE: 10

Ala Phe Trp Thr Glu Leu Trp
 1               5

<210> SEQ ID NO 11
<211> LENGTH: 21
<212> TYPE: DNA
<213> ORGANISM: Oryctolagus cuniculus

<400> SEQUENCE: 11
gcattctgga cagaactatg g                                                      21

<210> SEQ ID NO 12
<211> LENGTH: 21
<212> TYPE: DNA
<213> ORGANISM: Oryctolagus cuniculus

<400> SEQUENCE: 12
ccaaagttca gtccagaaag c                                                      21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
<221> NAME/KEY: unsure
<222> LOCATION: (4)
<221> NAME/KEY: unsure
<222> LOCATION: (10)
<221> NAME/KEY: unsure
<222> LOCATION: (19)

<400> SEQUENCE: 13
ccanagttcn gtccagaang c                                                      21

<210> SEQ ID NO 14
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
<221> NAME/KEY: unsure
<222> LOCATION: (10)
<221> NAME/KEY: unsure
<222> LOCATION: (19)

<400> SEQUENCE: 14
ccataattcn gtccagaang c                                              21

<210> SEQ ID NO 15
<211> LENGTH: 30
<212> TYPE: PRT
<213> ORGANISM: Oryctolagus cuniculus

<400> SEQUENCE: 15

Met Trp Leu Cys Ala Leu Ala Leu Ala Ser Leu Ala Ala Cys Thr Ala
  1               5                  10                  15

Trp Gly His Pro Ser Ala Pro Pro Val Val Asp Thr Val Lys
             20                  25                  30

<210> SEQ ID NO 16
<211> LENGTH: 30
<212> TYPE: PRT
<213> ORGANISM: Rattus sp.

<400> SEQUENCE: 16

Met Trp Leu Cys Ala Leu Val Trp Ala Ser Leu Ala Val Cys Pro Ile
  1               5                  10                  15

Trp Gly His Pro Ser Ser Pro Pro Val Val Asp Thr Thr Lys
             20                  25                  30

<210> SEQ ID NO 17
<211> LENGTH: 30
<212> TYPE: PRT
<213> ORGANISM: Homo sapiens

<400> SEQUENCE: 17

Met Trp Leu Arg Ala Phe Ile Leu Ala Thr Leu Ser Ala Ser Ala Ala
  1               5                  10                  15

Trp Gly His Pro Ser Ser Pro Pro Val Val Asp Thr Val His
             20                  25                  30

<210> SEQ ID NO 18
<211> LENGTH: 30
<212> TYPE: PRT
<213> ORGANISM: Rattus sp.

<400> SEQUENCE: 18

Met Arg Leu Tyr Pro Leu Val Trp Leu Phe Leu Ala Ala Cys Thr Ala
  1               5                  10                  15

Trp Gly Tyr Pro Ser Ser Pro Pro Val Val Asn Thr Val Lys
             20                  25                  30

<210> SEQ ID NO 19
<211> LENGTH: 30
<212> TYPE: PRT
<213> ORGANISM: Mus musculus

<400> SEQUENCE: 19

Met Trp Leu His Ala Leu Val Trp Ala Ser Leu Ala Val Cys Pro Ile
  1               5                  10                  15
```

Leu Gly His Ser Leu Leu Pro Pro Val Val Asp Thr Thr Gln
            20                  25                  30

<210> SEQ ID NO 20
<211> LENGTH: 1717
<212> TYPE: DNA
<213> ORGANISM: Oryctolagus cuniculus

<400> SEQUENCE: 20

| | | | | | |
|---|---|---|---|---|---|
| gaattctgcc | atgtggctct | gtgcattggc | cctggcctct | ctcgccgctt | gcacggcttg | 60 |
| ggggcacccg | tctgcaccac | ctgtggtaga | tactgtgcat | ggcaaagtcc | tggggaagtt | 120 |
| cgtcagctta | aaggatttg | cacagcccgt | ggccgtcttc | ctgggagtcc | ccttcgccaa | 180 |
| gcccctctt | ggatccctga | ggtttgcacc | accacagcct | gcagaatcat | tgagccacgt | 240 |
| gaagaacacc | acctcctacc | ctcccatgtg | ctcccaggac | gcagtatcag | ggcatatgct | 300 |
| ctcggagctc | ttcaccaaca | gaaaagagaa | catccctctt | aagttttctg | aagactgcct | 360 |
| ttacctgaat | atttacaccc | ctgctgacct | gacaaagaga | ggcaggctgc | cggtgatggt | 420 |
| gtggatccat | ggaggtggtc | tgatggtggg | tggagcatca | acctatgatg | gcctggctct | 480 |
| ttctgcccat | gagaacgtgg | tggtggtgac | cattcagtac | cgcctgggca | tctggggatt | 540 |
| cttcagcaca | ggagatgagc | acagccgagg | gaactgggt | cacttggacc | aggtggctgc | 600 |
| gctgcggtgg | gtccaggaca | cattgccaa | ctttggaggg | gacccaggct | ctgtgaccat | 660 |
| ctttggagag | tcagcaggag | gtcaaagtgt | ctctatcctt | ctattatccc | ccctgaccaa | 720 |
| gaatctcttc | catcgagcaa | tttccgagag | tggcgtggcc | ctccttttcca | gtctcttcag | 780 |
| gaagaacacc | aagtccttgg | ctgagaaaat | tgccatcgaa | gctgggtgta | aaaccaccac | 840 |
| ctcggctgtc | atggttcact | gcctgcgcca | aagacagag | gaagaactca | tggaggtgac | 900 |
| attgaaaatg | aaatttatgg | ctctagatct | agttggcgac | cccaaagaga | acaccgcctt | 960 |
| cctgaccact | gtgattgatg | gggtgctgct | gccaaaagca | cctgcagaga | ttctggcaga | 1020 |
| gaagaaatac | aacatgctgc | cctacatggt | gggaatcaac | cagcaagagt | ttggctggat | 1080 |
| tatcccaatg | caaatgctgg | gctatccact | ctctgaaggc | aaactggacc | agaagacagc | 1140 |
| tacagaactc | ttgtggaagt | cctacccat | tgtcaatgtc | tctaaggagc | tgactccagt | 1200 |
| ggccactgag | aagtatttag | gagggacaga | tgaccctgtc | aaaaagaaag | acttgttcct | 1260 |
| ggacatgctt | gcagatttgt | tattggtgt | cccatctgtg | aatgtggctc | gtcaccacag | 1320 |
| agatgctgga | gcccccacct | atatgtgata | gtatcggtat | cgcccaagct | tctcatcaga | 1380 |
| catgagaccc | aagacagtga | tgggggacca | tggagatgag | atcttctctg | tcttaggagc | 1440 |
| cccgtttta | aaagagggtg | ccacagaaga | ggagatcaaa | ctgagcaaga | tggtgatgaa | 1500 |
| atactgggcc | aactttgcta | ggaatgggaa | tcccaatgga | gaagggcttc | ctcaatggcc | 1560 |
| agcatatgac | tacaaggaag | gttacctgca | gattggagcc | accacccagg | cagcccagaa | 1620 |
| actgaaagac | aaggaagtgg | ctttctggac | tgagctctgg | gccaaggagg | cagcaaggcc | 1680 |
| acgtgagaca | gagcacattg | agctgtgaat | tgaattc | | | 1717 |

<210> SEQ ID NO 21
<211> LENGTH: 565
<212> TYPE: PRT
<213> ORGANISM: Oryctolagus cuniculus

<400> SEQUENCE: 21

Met Trp Leu Cys Ala Leu Ala Leu Ala Ser Leu Ala Ala Cys Thr Ala

-continued

|   1           |       |       |       | 5     |       |       |       | 10    |       |       |       | 15    |       |       |
|---------------|-------|-------|-------|-------|-------|-------|-------|-------|-------|-------|-------|-------|-------|-------|

Trp Gly His Pro Ser Ala Pro Pro Val Val Asp Thr Val His Gly Lys
            20                      25                      30

Val Leu Gly Lys Phe Val Ser Leu Glu Gly Phe Ala Gln Pro Val Ala
            35                      40                      45

Val Phe Leu Gly Val Pro Phe Ala Lys Pro Pro Leu Gly Ser Leu Arg
            50                      55                      60

Phe Ala Pro Pro Gln Pro Ala Glu Ser Trp Ser His Val Lys Asn Thr
65                      70                      75                      80

Thr Ser Tyr Pro Pro Met Cys Ser Gln Asp Ala Val Ser Gly His Met
            85                      90                      95

Leu Ser Glu Leu Phe Thr Asn Arg Lys Glu Asn Ile Pro Leu Lys Phe
            100                     105                     110

Ser Glu Asp Cys Leu Tyr Leu Asn Ile Tyr Thr Pro Ala Asp Leu Thr
            115                     120                     125

Lys Arg Gly Arg Leu Pro Val Met Val Trp Ile His Gly Gly Gly Leu
130                     135                     140

Met Val Gly Gly Ala Ser Thr Tyr Asp Gly Leu Ala Leu Ser Ala His
145                     150                     155                     160

Glu Asn Val Val Val Thr Ile Gln Tyr Arg Leu Gly Ile Trp Gly
            165                     170                     175

Phe Phe Ser Thr Gly Asp Glu His Ser Arg Gly Asn Trp Gly His Leu
            180                     185                     190

Asp Gln Val Ala Ala Leu Arg Trp Val Gln Asp Asn Ile Ala Asn Phe
            195                     200                     205

Gly Gly Asp Pro Gly Ser Val Thr Ile Phe Gly Glu Ser Ala Gly Gly
            210                     215                     220

Gln Ser Val Ser Ile Leu Leu Leu Ser Pro Leu Thr Lys Asn Leu Phe
225                     230                     235                     240

His Arg Ala Ile Ser Glu Ser Gly Val Ala Leu Leu Ser Ser Leu Phe
            245                     250                     255

Arg Lys Asn Thr Lys Ser Leu Ala Glu Lys Ile Ala Ile Glu Ala Gly
            260                     265                     270

Cys Lys Thr Thr Thr Ser Ala Val Met Val His Cys Leu Arg Gln Lys
            275                     280                     285

Thr Glu Glu Glu Leu Met Glu Val Thr Leu Lys Met Lys Phe Met Ala
            290                     295                     300

Leu Asp Leu Val Gly Asp Pro Lys Glu Asn Thr Ala Phe Leu Thr Thr
305                     310                     315                     320

Val Ile Asp Gly Val Leu Leu Pro Lys Ala Pro Ala Glu Ile Leu Ala
            325                     330                     335

Glu Lys Lys Tyr Asn Met Leu Pro Tyr Met Val Gly Ile Asn Gln Gln
            340                     345                     350

Glu Phe Gly Trp Ile Ile Pro Met Gln Met Leu Gly Tyr Pro Leu Ser
            355                     360                     365

Glu Gly Lys Leu Asp Gln Lys Thr Ala Thr Glu Leu Leu Trp Lys Ser
            370                     375                     380

Tyr Pro Ile Val Asn Val Ser Lys Glu Leu Thr Pro Val Ala Thr Glu
385                     390                     395                     400

Lys Tyr Leu Gly Gly Thr Asp Asp Pro Val Lys Lys Asp Leu Phe
            405                     410                     415

Leu Asp Met Leu Ala Asp Leu Leu Phe Gly Val Pro Ser Val Asn Val
            420                     425                     430

```
Ala Arg His His Arg Asp Ala Gly Ala Pro Thr Tyr Met Tyr Glu Tyr
        435                 440                 445

Arg Tyr Arg Pro Ser Phe Ser Ser Asp Met Arg Pro Lys Thr Val Ile
        450                 455                 460

Gly Asp His Gly Asp Glu Ile Phe Ser Val Leu Gly Ala Pro Phe Leu
465                 470                 475                 480

Lys Glu Gly Ala Thr Glu Glu Ile Lys Leu Ser Lys Met Val Met
                485                 490                 495

Lys Tyr Trp Ala Asn Phe Ala Arg Asn Gly Asn Pro Asn Gly Glu Gly
                500                 505                 510

Leu Pro Gln Trp Pro Ala Tyr Asp Tyr Lys Glu Gly Tyr Leu Gln Ile
        515                 520                 525

Gly Ala Thr Thr Gln Ala Ala Gln Lys Leu Lys Asp Lys Glu Val Ala
        530                 535                 540

Phe Trp Thr Glu Leu Trp Ala Lys Glu Ala Ala Arg Pro Arg Glu Thr
545                 550                 555                 560

Glu His Ile Glu Leu
                565

<210> SEQ ID NO 22
<211> LENGTH: 6
<212> TYPE: DNA
<213> ORGANISM: Artificial Sequence
<220> FEATURE:
<223> OTHER INFORMATION: Description of Artificial Sequence: Synthetic

<400> SEQUENCE: 22 cacgtg                                                                    6

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Synthetic

<400> SEQUENCE: 23
ggcaggaatt ctgccatgtg gctctg                                             26

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Synthetic

<400> SEQUENCE: 24
cgggaattca cattcacagc tcaatgt                                            27

<210> SEQ ID NO 25
<211> LENGTH: 6
<212> TYPE: DNA
<213> ORGANISM: Artificial Sequence
<220> FEATURE:
<223> OTHER INFORMATION: Description of Artificial Sequence: Synthetic

<400> SEQUENCE: 25 cacctg                                                                    6

<210> SEQ ID NO 26
<211> LENGTH: 543
```

```
<212> TYPE: PRT
<213> ORGANISM: Oryctolagus cuniculus

<400> SEQUENCE: 26

Met Trp Leu Cys Ala Leu Ala Leu Ala Ser Leu Ala Ala Cys Thr Ala
  1               5                  10                  15

Trp Gly His Pro Ser Ala Pro Pro Val Val Asp Thr Val His Gly Lys
                 20                  25                  30

Val Leu Gly Lys Phe Val Ser Leu Glu Gly Phe Ala Gln Pro Val Ala
             35                  40                  45

Val Phe Leu Gly Val Pro Phe Ala Lys Pro Pro Leu Gly Ser Leu Arg
 50                  55                  60

Phe Ala Pro Gln Pro Ala Glu Ser Trp Ser His Val Lys Asn Thr
 65                  70                  75                  80

Thr Ser Tyr Pro Pro Met Cys Ser Gln Asp Ala Val Ser Gly His Met
                 85                  90                  95

Leu Ser Glu Leu Phe Thr Asn Arg Lys Glu Asn Ile Pro Leu Lys Phe
            100                 105                 110

Ser Glu Asp Cys Leu Tyr Leu Asn Ile Tyr Thr Pro Ala Asp Leu Thr
            115                 120                 125

Lys Arg Gly Arg Leu Pro Val Met Val Trp Ile His Gly Gly Gly Leu
130                 135                 140

Met Val Gly Gly Ala Ser Thr Tyr Asp Gly Leu Ala Leu Ser Ala His
145                 150                 155                 160

Glu Asn Val Val Val Thr Ile Gln Tyr Arg Leu Gly Ile Trp Gly
                165                 170                 175

Phe Phe Ser Thr Gly Asp Glu His Ser Arg Gly Asn Trp Gly His Leu
                180                 185                 190

Asp Gln Val Ala Ala Leu Arg Trp Val Gln Asp Asn Ile Ala Asn Phe
            195                 200                 205

Gly Gly Asp Pro Gly Ser Val Thr Ile Phe Gly Glu Ser Ala Gly Gly
            210                 215                 220

Gln Ser Val Ser Ile Leu Leu Ser Pro Leu Thr Lys Asn Leu Phe
225                 230                 235                 240

His Arg Ala Ile Ser Glu Ser Gly Val Ala Leu Leu Ser Ser Leu Phe
                245                 250                 255

Arg Lys Asn Thr Lys Ser Leu Ala Glu Lys Ile Ala Ile Glu Ala Gly
            260                 265                 270

Cys Lys Thr Thr Thr Ser Ala Val Met Val His Cys Leu Arg Gln Lys
            275                 280                 285

Thr Glu Glu Glu Leu Met Glu Val Thr Leu Lys Met Lys Phe Met Ala
            290                 295                 300

Leu Asp Leu Val Gly Asp Pro Lys Glu Asn Thr Ala Phe Leu Thr Thr
305                 310                 315                 320

Val Ile Asp Gly Val Leu Leu Pro Lys Ala Pro Ala Glu Ile Leu Ala
                325                 330                 335

Glu Lys Lys Tyr Asn Met Leu Pro Tyr Met Val Gly Ile Asn Gln Gln
            340                 345                 350

Glu Phe Gly Trp Ile Ile Pro Met Gln Met Leu Gly Tyr Pro Leu Ser
            355                 360                 365

Glu Gly Lys Leu Asp Gln Lys Thr Ala Thr Glu Leu Leu Trp Lys Ser
            370                 375                 380

Tyr Pro Ile Val Asn Val Ser Lys Glu Leu Thr Pro Val Ala Thr Glu
385                 390                 395                 400
```

```
Lys Tyr Leu Gly Gly Thr Asp Asp Pro Val Lys Lys Asp Leu Phe
                405                 410                 415
Leu Asp Met Leu Ala Asp Leu Leu Phe Gly Val Pro Ser Val Asn Val
            420                 425                 430
Ala Arg His His Arg Asp Ala Gly Ala Pro Thr Tyr Met Tyr Glu Tyr
        435                 440                 445
Arg Tyr Arg Pro Ser Phe Ser Ser Asp Met Arg Pro Lys Thr Val Ile
    450                 455                 460
Gly Asp His Gly Asp Glu Ile Phe Ser Val Leu Gly Ala Pro Phe Leu
465                 470                 475                 480
Lys Glu Gly Ala Thr Glu Glu Ile Lys Leu Ser Lys Met Val Met
            485                 490                 495
Lys Tyr Trp Ala Asn Phe Ala Arg Asn Gly Asn Pro Asn Gly Glu Gly
            500                 505                 510
Leu Pro Gln Trp Pro Ala Tyr Asp Tyr Lys Glu Gly Tyr Leu Gln Ile
        515                 520                 525
Gly Ala Thr Thr Gln Ala Ala Gln Lys Leu Lys Asp Lys Glu Val
    530                 535                 540

<210> SEQ ID NO 27
<211> LENGTH: 2191
<212> TYPE: DNA
<213> ORGANISM: Homo sapiens

<400> SEQUENCE: 27
tcgagcggcc acccgggcag gtctctgggt gaatagcagc gtgtccgccg gcagcgaacc      60
gagaccagcg agccgaccat gcggctgcac agacttcgtg cgcggctgag cgcggtggcc     120
tgtgggcttc tgctgcttct tgtccggggc cagggccagg actcagccag tcccatccgg     180
accacacaca cggggcaggt gctggggagt cttgtccatg tgaagggcgc caatgccggg     240
gtccaaacct tcctgggaat tccatttgcc aagccacctc taggtccgct gcgatttgca     300
ccccctgagc ccctgaatc ttggagtggt gtgagggatg gaaccaccca tccggccatg     360
tgtctacagg acctcaccgc agtggagtca gagtttctta gccagttcaa catgaccttc     420
ccttccgact ccatgtctga ggactgcctg tacctcagca tctacacgcc ggcccatagc     480
catgaaggct ctaacctgcc ggtgatggtg tggatccacg gtggtgcgct tgttttttggc     540 atggcttcct gtatgatgg ttccatgctg gctgccttgg agaacgtggt ggtggtcatc     600
atccagtacc gcctgggtgt cctgggcttc ttcagcactg gagacaagca cgcaaccggc     660 aactgggggct acctggacca agtggctgca ctacgctggg tccagcagaa tatcgcccac     720 tttgaggca ccctgaccg tgtcaccatt tttggcgagt ctgcgggtgg cacgagtgtg     780
tcttcgcttg ttgtgtcccc catatcccaa ggactcttcc acggagccat catggagagt     840
ggcgtggccc cctgcccgg cctcattgcc agctcagctc atgtcatctc cacggtggtg     900
gccaacctgt ctgcctgtga ccaagttgac tctgaggccc tggtgggctg cctgcggggc     960
aagagtaaag aggagattct tgcaattaac aagccttttca agatgatccc cggagtggtg    1020
gatggggtct tcctgcccag gcacccccag gagctgctgg cctctgccga ctttcagcct    1080
gtccctagca ttgttggtgt caacaacaat gaattcggct ggctcatccc caaggtcatg    1140
aggatctatg ataccagaa ggaaatggac agagaggcct cccaggctgc tctgcagaaa    1200
atgttaacgc tgctgatgtt gcctcctaca tttggtgacc tgctgaggga ggagtacatt    1260
ggggacaatg gggatcccca gaccctccaa gcgcagttcc aggagatgat ggcggactcc    1320
```

-continued

```
atgtttgtga tccctgcact ccaagtagca cattttcagt gttcccgggc ccctgtgtac    1380
ttctacgagt tccagcatca gcccagctgg ctcaagaaca tcaggccacc gcacatgaag    1440
gcagaccatg gtgatgagct tccttttgtt ttcagaagtt tctttggggg caactacatt    1500
aaattcactg aggaagagga gcagctaagc aggaagatga tgaagtactg gccaactttt    1560
gcgagaaatg ggaaccccaa tggcgagggt ctgccacact ggccgctgtt cgaccaggag    1620
gagcaatacc tgcagctgaa cctacagcct gcggtgggcc gggctctgaa ggcccacagg    1680
ctccagttct ggaagaaggc gctgccccaa aagatccagg agctcgagga gcctgaagag    1740
agacacacag agctgtagct ccctgtgccg gggaggaggg ggtgggttcg ctgacaggcg    1800
agggtcagcc tgctgtgccc acacacaccc actaaggaga aagaagttga ttccttcatt    1860
cacttcgcca ttcattcata cttccgtcca gaagttgatt ccttcattca cttcgccatt    1920
cattcatact tccgtccatc cattcagaaa ccggyattta ttaagaattt actcaggcat    1980
gatggcccat acttgtaatc ccagctattg ggaaggatga gatgggagga tggcttgagg    2040
ccagaggttt gagaccgacc agccagggca acacagtgag accccttctc aaaaaaaaaa    2100
aaaaaaaaag agagagtgtg tgattagaag ctaaatagga aagttttgag cttcaagtca    2160
gtgaggagta aaaagatttt ttaaaaagca a                                   2191
```

<210> SEQ ID NO 28
<211> LENGTH: 559
<212> TYPE: PRT
<213> ORGANISM: Homo sapiens

<400> SEQUENCE: 28

```
Met Arg Leu His Arg Leu Arg Ala Arg Leu Ser Ala Val Ala Cys Gly
  1               5                  10                  15

Leu Leu Leu Leu Leu Val Arg Gly Gln Gly Gln Asp Ser Ala Ser Pro
                 20                  25                  30

Ile Arg Thr Thr His Thr Gly Gln Val Leu Gly Ser Leu Val His Val
             35                  40                  45

Lys Gly Ala Asn Ala Gly Val Gln Thr Phe Leu Gly Ile Pro Phe Ala
         50                  55                  60

Lys Pro Pro Leu Gly Pro Leu Arg Phe Ala Pro Pro Glu Pro Pro Glu
 65                  70                  75                  80

Ser Trp Ser Gly Val Arg Asp Gly Thr Thr His Pro Ala Met Cys Leu
                 85                  90                  95

Gln Asp Leu Thr Ala Val Glu Ser Glu Phe Leu Ser Gln Phe Asn Met
            100                 105                 110

Thr Phe Pro Ser Asp Ser Met Ser Glu Asp Cys Leu Tyr Leu Ser Ile
        115                 120                 125

Tyr Thr Pro Ala His Ser His Glu Gly Ser Asn Leu Pro Val Met Val
    130                 135                 140

Trp Ile His Gly Gly Ala Leu Val Phe Gly Met Ala Ser Leu Tyr Asp
145                 150                 155                 160

Gly Ser Met Leu Ala Ala Leu Glu Asn Val Val Val Ile Ile Gln
                165                 170                 175

Tyr Arg Leu Gly Val Leu Gly Phe Phe Ser Thr Gly Asp Lys His Ala
            180                 185                 190

Thr Gly Asn Trp Gly Tyr Leu Asp Gln Val Ala Ala Leu Arg Trp Val
        195                 200                 205

Gln Gln Asn Ile Ala His Phe Gly Gly Asn Pro Asp Arg Val Thr Ile
```

```
              210                 215                 220
Phe Gly Glu Ser Ala Gly Gly Thr Ser Val Ser Ser Leu Val Val Ser
225                 230                 235                 240

Pro Ile Ser Gln Gly Leu Phe His Gly Ala Ile Met Glu Ser Gly Val
                245                 250                 255

Ala Leu Leu Pro Gly Leu Ile Ala Ser Ser Ala Asp Val Ile Ser Thr
                260                 265                 270

Val Val Ala Asn Leu Ser Ala Cys Asp Gln Val Asp Ser Glu Ala Leu
                275                 280                 285

Val Gly Cys Leu Arg Gly Lys Ser Lys Glu Glu Ile Leu Ala Ile Asn
                290                 295                 300

Lys Pro Phe Lys Met Ile Pro Gly Val Val Asp Gly Val Phe Leu Pro
305                 310                 315                 320

Arg His Pro Gln Glu Leu Leu Ala Ser Ala Asp Phe Gln Pro Val Pro
                325                 330                 335

Ser Ile Val Gly Val Asn Asn Asn Glu Phe Gly Trp Leu Ile Pro Lys
                340                 345                 350

Val Met Arg Ile Tyr Asp Thr Gln Lys Glu Met Asp Arg Glu Ala Ser
                355                 360                 365

Gln Ala Ala Leu Gln Lys Met Leu Thr Leu Leu Met Leu Pro Pro Thr
                370                 375                 380

Phe Gly Asp Leu Leu Arg Glu Glu Tyr Ile Gly Asp Asn Gly Asp Pro
385                 390                 395                 400

Gln Thr Leu Gln Ala Gln Phe Gln Glu Met Met Ala Asp Ser Met Phe
                405                 410                 415

Val Ile Pro Ala Leu Gln Val Ala His Phe Gln Cys Ser Arg Ala Pro
                420                 425                 430

Val Tyr Phe Tyr Glu Phe Gln His Gln Pro Ser Trp Leu Lys Asn Ile
                435                 440                 445

Arg Pro Pro His Met Lys Ala Asp His Gly Asp Glu Leu Pro Phe Val
                450                 455                 460

Phe Arg Ser Phe Phe Gly Gly Asn Tyr Ile Lys Phe Thr Glu Glu Glu
465                 470                 475                 480

Glu Gln Leu Ser Arg Lys Met Met Lys Tyr Trp Ala Asn Phe Ala Arg
                485                 490                 495

Asn Gly Asn Pro Asn Gly Glu Gly Leu Pro His Trp Pro Leu Phe Asp
                500                 505                 510

Gln Glu Glu Gln Tyr Leu Gln Leu Asn Leu Gln Pro Ala Val Gly Arg
                515                 520                 525

Ala Leu Lys Ala His Arg Leu Gln Phe Trp Lys Lys Ala Leu Pro Gln
                530                 535                 540

Lys Ile Gln Glu Leu Glu Glu Pro Glu Glu Arg His Thr Glu Leu
545                 550                 555

<210> SEQ ID NO 29
<211> LENGTH: 31
<212> TYPE: DNA
<213> ORGANISM: Artificial Sequence
<220> FEATURE:
<223> OTHER INFORMATION: Description of Artificial Sequence: Synthetic

<400> SEQUENCE: 29
cggtctagag agctacagct ctgtgtgtct g                                 31

<210> SEQ ID NO 30
```

-continued

```
<211> LENGTH: 31
<212> TYPE: DNA
<213> ORGANISM: Artificial Sequence
<220> FEATURE:
<223> OTHER INFORMATION: Description of Artificial Sequence: Synthetic

<400> SEQUENCE: 30
cgagtctaga gagccgacca tgcggctgca c                           31
```

COMPOSITIONS AND METHODS FOR SENSITIZING AND INHIBITING GROWTH OF HUMAN TUMOR CELLS

This application is a continuation-in-part of PCT/US99/03171 filed Feb. 12, 1999, which claims the benefit of priority from provisional U.S. Application Serial No. 60/075,258, filed Feb. 19, 1998.

This invention was supported in part by funds from the U.S. Government NIH Grant Nos. CA-66124 and CA-63512 and the U.S. Government may therefore have certain rights in the invention.

Introduction

1. Field of the Invention

This invention relates to novel polynucleotides identified and sequenced which encode a carboxylesterase enzyme, polypeptides encoded by these polynucleotides and vectors and host cells comprising these vectors which express the enzyme. This enzyme is capable of metabolizing chemotherapeutic prodrugs and inactive metabolites into active drug. The instant invention thus relates to compositions comprising these polynucleotides and methods for sensitizing selected tumor cells to a chemotherapeutic prodrug by transfecting the tumor cells with a polynucleotide placed under the control of a disease-specific responsive promoter. Sensitized tumor cells can then be contacted with a chemotherapeutic prodrug to inhibit tumor cell growth. Compositions of the present invention can also be used in combination with chemotherapeutic prodrugs to purge bone marrow of tumor cells. The invention further includes novel drug screening assays for identifying chemotherapeutic prodrugs that are activated by this enzyme.

2. Background of the Invention

Cancer is a disease resulting from multiple changes at the genomic level. These changes ultimately lead to the malfunction of cell cycle machinery and finally to autonomous cell proliferation. Neoplastic transformation involves four types of genes: oncogenes, tumor-suppressor genes, mutator genes, and apoptotic genes. Different types of cancer can involve alteration of any one or any combination of these genes.

Proto-oncogenes of the myc family are overexpressed in many different types of human tumors including tumors of the breast, colon, cervix, head and neck, and brain. Many solid tumors amplify or overexpress c-myc, with up to a 50-fold increase in c-myc RNA in tumor cells relative to normal cells having been reported (Yamada, H. et al. 1986. *Jpn. J. Cancer Res.* 77:370–375). For example, three of the six most common solid tumors, including up to 100% of colon adenocarcinomas, 57% of breast cancers, and 35% of cervical cancers, demonstrate increased levels of c-myc protein. Enforced expression of c-myc in nontumorigenic cells causes immortalization but not transformation; however, elevated levels of c-myc protein are rare in benign cancers and normal differentiated tissue. While solid tumors can oftentimes be removed surgically, overexpression of c-myc has been linked with amplification of the c-myc gene and correlated with poor prognosis and an increased risk of relapse (Nagai, M. A. et al. 1992. *Dis. Colon Rectum* 35:444–451; Orian, J. M. et al. 1992. *Br. J. Cancer* 66:106–112; Riou, G. et al. 1987. *Lancet* 2:761–763; Field, J. K. et al. 1989. *Oncogene* 4:1463–1468).

Another member of the myc oncogene family, N-myc, has been linked with development of neuroblastomas in young children. Overexpression of this member of the myc family of proto-oncogenes has also been correlated with advanced stages of disease and poor prognosis (Brodeur, G. M. et al. 1997. *J. Ped. Hematol. Oncol.* 19:93–101). Primary tumors for this specific condition usually arise in the abdomen and as many as 70% of patients have bone marrow metastases at diagnosis (Matthay, K. E. 1997. *Oncology* 11:1857–1875). Treatment of children with Stage 4 disease using surgery, chemotherapy, and purged autologous or allogeneic marrow transplant produces a progression-free survival rate of 25 to 49% in patients four years post transplant (Matthay, K. K. et al. 1994. *J. Clin. Oncol.* 12:2382–2389). Most relapses after autotransplant occur at sites of bulk disease and/or previously involved sites. Estimates of the rate of local recurrence vary depending upon the study. However, recurrence of tumor at an original site has been estimated to occur in approximately 25% of high risk neuroblastoma patients.

Further, definitive evidence from gene marking studies indicates that autologous marrow, free of malignant cells by standard clinical and morphologic criteria, contributes to relapse at both medullary and extramedullary sites (Rill, D. R. et al. 1994. *Blood* 84:380–383). In a recent pilot clinical study, bone marrow involvement at diagnosis correlated with specific relapse at that site in children receiving autologous purged marrow (Matthay, K. K. et al. 1993. *J. Clin. Oncol.* 11:2226–2233). Accordingly, improvements in surgery, detection of tumor margins, development of new anticancer drugs or application of novel therapies are required to prevent local tumor regrowth. In particular, more effective treatment strategies are needed for elimination of "minimal residual disease" or "MRD" which results from the presence of a small number of tumor cells at the site of disease after treatments such as tumor resection or purging bone marrow of tumor cells.

CPT-11 (irinotecan, 7-ethyl-10-[4-(1-piperidino)-1-piperidino]carbonyloxycamptothecin) is a prodrug currently under investigation for the treatment of cancer that is converted to the active drug known as SN-38 (7-ethyl-10-hydroxy-camptothecin) (Tsuji, T. et al. 1991. *J. Pharmacobiol. Dynamics* 14:341–349; Satoh, T. et al. 1994. *Biol. Pharm. Bull.* 17:662–664). SN-38 is a potent inhibitor of topoisomerase I (Tanizawa, A. et al. 1994. *J. Natl. Cancer Inst.* 86:836–842; Kawato, Y. et al. 1991. *Cancer Res.* 51:4187–4194), an enzyme whose inhibition in cells can result in DNA damage and induction of apoptosis (Hsiang, Y. -H. et al. 1989. *Cancer Res.* 49:5077–5082). The specific enzyme responsible for activation in vivo of CPT-11 has not been identified, although serum or liver homogenates from several mammalian species have been shown to contain activities that convert CPT-11 to SN-38 (Tsuji, T. et al. 1991. *J. Pharmacobiol. Dynamics* 14:341–349; Senter, P. D. et al. 1996. *Cancer Res.* 56:1471–1474; Satoh, T. et al. 1994. *Biol. Pharm. Bull.* 17:662–664). Uniformly, these activities have characteristics of carboxylesterase (CE) enzymes (Tsuji, T. et al. 1991. *J. Pharmacobiol. Dynamics* 14:341–349; Senter, P. D. et al. 1996. *Cancer Res.* 56:1471–1474; Satoh, T. et al. 1994. *Biol. Pharm. Bull.* 17:662–664). In fact, SN-38 can be detected in the plasma of animals and humans minutes after the administration of CPT-11 (Stewart, C. F. et al. 1997. *Cancer Chemother. Pharmacol.* 40:259–265; Kaneda, N. et al. 1990. *Cancer Res.* 50:1715–1720; Rowinsky, E. K. et al. 1994. *Cancer Res.* 54:427–436), suggesting that a CE enzyme present in either serum or tissues can convert the camptothecin analog to its active metabolite.

CEs are ubiquitous serine esterase enzymes that are thought to be involved in the detoxification of a variety of xenobiotics. CEs are primarily present in liver and serum, however, the physiological role of this class of enzymes has yet to be identified. A recent biochemical analysis of 13 CEs compared their ability to metabolize CPT-11 to SN-38. While the efficiency of conversion varied between enzymes, those isolated from rodents were the most efficient (Satoh, T. et al. 1994. *Biol. Pharm. Bull.* 17:662–664). The amino acid sequence of a rabbit liver CE has been disclosed (Korza, G. and J. Ozols. 1988. *J. Biol. Chem.* 263:3486–3495). In addition, there are currently 13 CDNA sequences encoding CE in the GenBank and EMBL databases, including a rat serum and rat liver microsomal CE. Interestingly, CEs purified from human tissues demonstrated the least efficient conversion of CPT-11 to SN-38, with less than 5% of the prodrug being converted to active drug (Leinweber, F. J. 1987. *Drug Metab. Rev.* 18:379–439; Rivory, L. P. et al. 1997. *Clin. Cancer Res.* 3:1261–1266).

In addition to metabolism to SN-38, in humans CPT-11 is also metabolized to a compound known as APC (Haaz, M. C. et al. 1998. *Cancer Res.* 58:468–472). APC has little, if any, anti-tumor activity and is not converted to an active metabolite in humans (Rivory, L. P. et al. 1996. *Cancer Res.* 56:3689–3694).

In preclinical studies, CPT-11 administered to immune-deprived mice bearing human tumor xenografts produces complete regression of glioblastomas, rhabdomyosarcomas (RMS), neuroblastomas, and colon adenocarcinomas (Houghton, P. J. et al. 1995. *Cancer Chemother. Pharmacol.* 36:393–403; Houghton, P. J. et al. 1993. *Cancer Res.* 53:2823–2829). However, maintenance of tumor regression in studies with CPT-11 appears to be dependent upon drug scheduling, suggesting that viable tumor cells survive therapy (i.e., minimal residual disease (MRD)). These studies also showed a steep dose-response relationship between dose of drug administered and induction of tumor regression. For example, 20 mg of CPT-11/kg/day given daily for 5 days for two weeks produced complete regression of Rh18 RMS xenografts, while 10 mg/kg/day given on the same schedule produced only partial tumor regression. Similar effects were seen when mice bearing SJGC3A colon adenocarcinoma xenografts were treated with 40 mg CPT-11/kg compared to a 20 mg/kg dose.

Early clinical trials with CPT-11 indicate that the prodrug also has anti-tumor activity in vivo against many different types of solid tumors in humans. However, myelosuppression and secretory diarrhea limit the amount of drug that can be administered to patients. Accordingly, before this promising anti-cancer agent can be used successfully, these dose-limiting toxicities must be overcome.

The development of new effective treatment strategies for cancer is dependent upon the availability of specific drug screening assays. Specific drug screening assays can involve isolated target tissue models, i.e., isolated heart, ileum, vasculature, or liver from animals such as rabbits, rats, and guinea pigs, wherein the target tissue is removed from the animal and a selected activity of that target tissue is measured both before and after exposure to the candidate drug. An example of a selected activity measured in drug screening assays to identify new cancer agents is the activity of enzymes such as topoisomerase I or II, which are known to modulate cell death. Such assays can also be used to screen for potential prodrugs which are converted to the active metabolite in selected tissues or to identify selected tissues capable of converting prodrug to its active metabolite.

However, any molecular event that is shown to be modified by a novel class of compounds can be developed as a screening assay for selection of the most promising compounds for therapeutic development. In fact, in recent years the idea of modulating cells at the genomic level has been applied to the treatment of diseases such as cancer. Gene therapy for treatment of cancer has been the focus of multiple clinical trials approved by the National Institutes of Health Recombinant DNA Advisory Committee, many of which have demonstrated successful clinical application (Hanania et al. 1995. *Am. Jour. Med.* 99:537–552; Johnson et al. 1995. *J. Am. Acad. Derm.* 32(5):689–707; Barnes et al. 1997. *Obstetrics and Gynecology* 89:145–155; Davis et al. 1996. *Current Opinion in Oncology* 8:499–508; Roth and Cristiano 1997. *J. Natl. Canc. Inst.* 89(1):21–39). To specifically target malignant cells and spare normal tissue, cancer gene therapies must combine selective gene delivery with specific gene expression, specific gene product activity, and, possibly, specific drug activation. Significant progress has been made in recent years using both viral (retrovirus, adenovirus, adeno-associated virus) and nonviral (liposomes, gene gun, injection) methods to efficiently deliver DNA to tumor sites. Genes can be transfected into cells by physical means such as scrape loading or ballistic penetration, by chemical means such as coprecipitation of DNA with calcium phosphate or liposomal encapsulation; or by electro-physiological means such as electroporation. The most widely used methods, however, involve transduction of genes by means of recombinant viruses, taking advantage of the relative efficiency of viral infection processes. Current methods of gene therapy involve infection of organisms with replication-deficient recombinant viruses containing the desired gene. The replication-deficient viruses most commonly used include retroviruses, adenoviruses, adeno-associated viruses, lentiviruses and herpes viruses. The efficacy of viral-mediated gene transfer can approach 100%, enabling the potential use of these viruses for the transduction of cells in vivo.

Adenovirus vector systems in particular have several advantages. These include the fact that non-dividing cells can be transduced; transduced DNA does not integrate into host cell DNA, thereby negating insertional mutagenesis; the design of adenoviral vectors allows up to 7 kb of foreign DNA to be incorporated into the viral genome; very high viral titers can be achieved and stored without loss of infectivity; and appropriate plasmids and packaging cell lines are available for the rapid generation of infectious, replication-deficient virus (Yang, N. S. 1992. *Crit. Rev. Biotechnol.* 12:335–356). The effectiveness of adenoviral-mediated delivery of genes into mammalian cells in culture and in animals has been demonstrated.

To increase the specificity and safety of gene therapy for treatment of cancer, expression of the therapeutic gene within the target tissue must also be tightly controlled. For tumor treatment, targeted gene expression has been analyzed using tissue-specific promoters such as breast, prostate and melanoma specific promoters and disease-specific responsive promoters such as carcinoembryonic antigen, HER-2/ neu, Myc-Max response elements, DF3/MUC. Dachs, D. U. et al. 1997. *Oncol. Res.* 9(6–7):313–25. For example, the utility of herpes simplex virus thymidine kinase (HSV-TK) gene ligated with four repeats of the Myc-Max response element, CACGTG (SEQ ID NO:22), as a gene therapy agent for treatment of lung cancer with ganciclovir was examined in c-, L- or N-myc-overexpressing small cell lung cancer (SCLC) cell lines (Kumagai, T. et al. 1996. *Cancer Res.* 56(2):354–358). Transduction of the HSV-TK gene ligated to this CACGTG (SEQ ID NO:22) core rendered individual clones of all three SCLC lines more sensitive to ganciclovir than parental cells in vitro, thus suggesting that a CACGTG-driven HSV-TK gene may be useful for the treatment of SCLC overexpressing any type of myc family oncogene. Additional experiments with c-myc have focused on the use of the ornithine decarboxylase (ODC) promoter gene. Within the first intron of the ODC gene are two CACGTG "E boxes" that provide binding sites for the c-myc protein when bound to its partner protein known as max. Mutation of the E box sequence results in the inability of c-myc to transactivate the ODC promoter. Previous reports indicate that reporter constructs containing the ODC promoter fused upstream of the chloramphenicol acetyl- transferase gene immediately adjacent to the second exon were activated in cells that overexpress c-myc (Bello- Fernandez, C. et al. 1993. *Proc. Natl Acad. Sci. USA* 90:7804–7808). In contrast, transient transfection of pro- moter constructs in which the E boxes were mutated (CACGTG (SEQ ID NO:22) to CACCTG (SEQ ID NO:25) demonstrate significantly lower reporter gene activity. These data suggest that it is possible to activate transcription of specific genes under control of the c-myc responsive ODC promoter. In the case of N-myc, N-myc protein is a basic helix-loop-helix (BHLH) protein that can dimerize with proteins of the same class. N-myc dimerizes with the BHLH protein max to form a complex that binds to the CACGTG motif present in gene promoters, such as ODC, resulting in transactivation and expression of specific genes containing this sequence (Lutz, W. et al. 1996. *Oncogene* 13:803–812). Studies in a neuroblastoma cell line and tumors have shown that binding of N-myc to its consensus DNA binding sequence correlates with N-myc expression, data that indi- cate that the level of N-myc in neuroblastoma cells is a determining factor in expression of proteins under control of promoters containing the CACGTG sequence (Raschella, G. et al. 1994. *Cancer Res.* 54:2251–2255). Inhibition of expression of the c-myc gene via antisense oligonucleotides as a means for inhibiting tumor growth has also been disclosed (Kawasaki, H. et al. 1996. *Artif. Organs* 20(8) :836–48).

In the present invention, polynucleotides encoding car- boxylesterase enzymes or active fragments thereof and polypeptides encoded thereby which are capable of metabo- lizing the chemotherapeutic prodrug CPT-11 and its inactive metabolite APC to active drug SN-38 are disclosed. Use of these enzymes in combination with APC renders this inac- tive metabolite a useful chemotherapeutic prodrug. It has also been found that compositions comprising a polynucle- otide of the present invention and a disease-specific respon- sive promoter can be delivered to selected tumor cells to sensitize the tumor cells to the chemotherapeutic prodrug CPT-11, thereby inhibiting tumor cell growth.

SUMMARY OF THE INVENTION

An object of the present invention is to provide poly- nucleotides encoding carboxylesterases capable of metabo- lizing a chemotherapeutic prodrug and inactive metabolites thereof to active drug.

Another object of the present invention it to provide polypeptides encoded by these polynucleotides.

Another object of the present invention is to provide vectors comprising these polynucleotides and host cells containing these vectors which express carboxylesterases.

Another object of the present invention is to provide a composition comprising a polynucleotide encoding a car- boxylesterase and a disease-specific responsive promoter of selected tumor cells or a promoter such as CMV.

Another object of the present invention is to provide a method for sensitizing tumor cells to a chemotherapeutic prodrug which comprises transfecting selected tumor cells with a composition comprising a polynucleotide encoding carboxylesterase and a disease-specific responsive promoter of the selected tumor cells.

Another object of the present invention is to provide a method of inhibiting growth of selected tumor cells which comprises sensitizing selected tumor cells to a chemothera- peutic prodrug metabolized to active drug by a carboxy- lesterase and administering a chemotherapeutic prodrug.

Another object of the present invention is to provide a method of using APC as a prodrug in the treatment of cancer.

Another object of the present invention is to provide drug screening assays for identification of compounds activated by carboxylesterases.

Yet another object of the present invention is to provide a modified ornithine decarboxylase promoter which upregu- lates target protein expression in tumor cells that over- express myc proteins.

BRIEF DESCRIPTION OF THE FIGURES

FIG. 1 shows the alignment of the amino acid sequences of a rabbit liver carboxylesterase (Rab; GenBank Accession # AF036930), a human liver carboxylesterase (hCE1; Gen- Bank Accession # M73499) and the human intestinal car- boxylesterase (hiCE; GenBank Accession # Y09616). The active site triad (Ser-240, Glu-364 and His-478) are indi- cated by an asterisk (*). Identical residues are indicated by a vertical line (|), conservative changes by a colon (:), semi-conservative changes by a period (.), and computer inserted gaps within the amino acids are indicated by a dash (-). Large areas of homology between all three proteins are shaded.

FIG. 2 shows the design of the oligonucleotides used for degenerate PCR. The amino acid sequence (SEQ ID NO:6) and the coding sequence (SEQ ID NO:7) of residues 1 through 5 of rabbit CE are depicted along with the corre- sponding oligonucleotide Rab51 (SEQ ID NO:8) and Rab52 (SEQ ID NO:9). Also depicted are the amino acid sequence (SEQ ID NO:10), the coding sequence (SEQ ID NO:11) and the reverse complement (SEQ ID NO:12) of residues 518 through 524 of rabbit CE, along with oligonucleotide Rab31 (SEQ ID NO:13) and Rab32 (SEQ ID NO:14).

FIG. 3 shows the alignment of N-terminal signal sequences of the rabbit liver CE (SEQ ID NO:15) and other known CEs including rat (P10959; SEQ ID NO:16), human (P23141; SEQ ID NO:17), rat (16303; SEQ ID NO:18) and mouse (P23953;

SEQ ID NO:19). Residues common to all CEs are under- lined and the 18 residue leader sequence is indicated in italics. The Swissprot Accession numbers are indicated in parentheses.

FIG. 4 shows the complete coding sequence of the rabbit liver CE (SEQ ID NO:20) and the amino acid sequence encoded thereby (SEQ ID NO:21). The 1698 bp ORF encodes a 62.3 kDa protein. The N-terminal hydrophobic leader sequence is in italics, the 5' and 3' RACE sequences are underlined and the potential active site serine is indicated by an asterisk. The carboxylesterase B-1 and B-2 motifs, at amino acids 208–223 and 114–124 are double underlined. Numbers over the sequence refer to nucleotide position whereas numbers along the left margin refer to amino acid residues.

Figure 5:
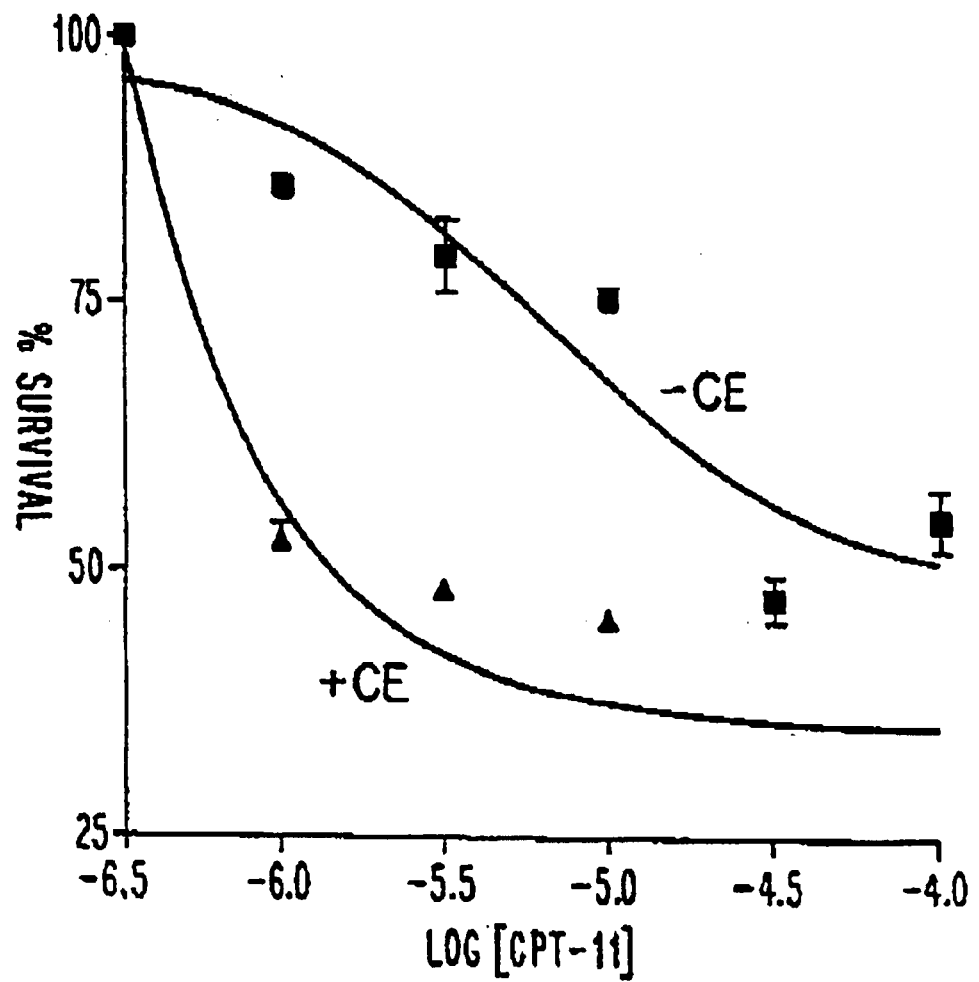

FIG. 5 is a linegraph comparing % cell survival, depicted on the Y-axis, at various concentrations of CPT-11, depicted on the X-axis. Control Cos7 cells (filled squares) are approximately 350-fold more sensitive to CPT-11 than Cos7 cell transfected with CE (filled triangles).

Figure 6:
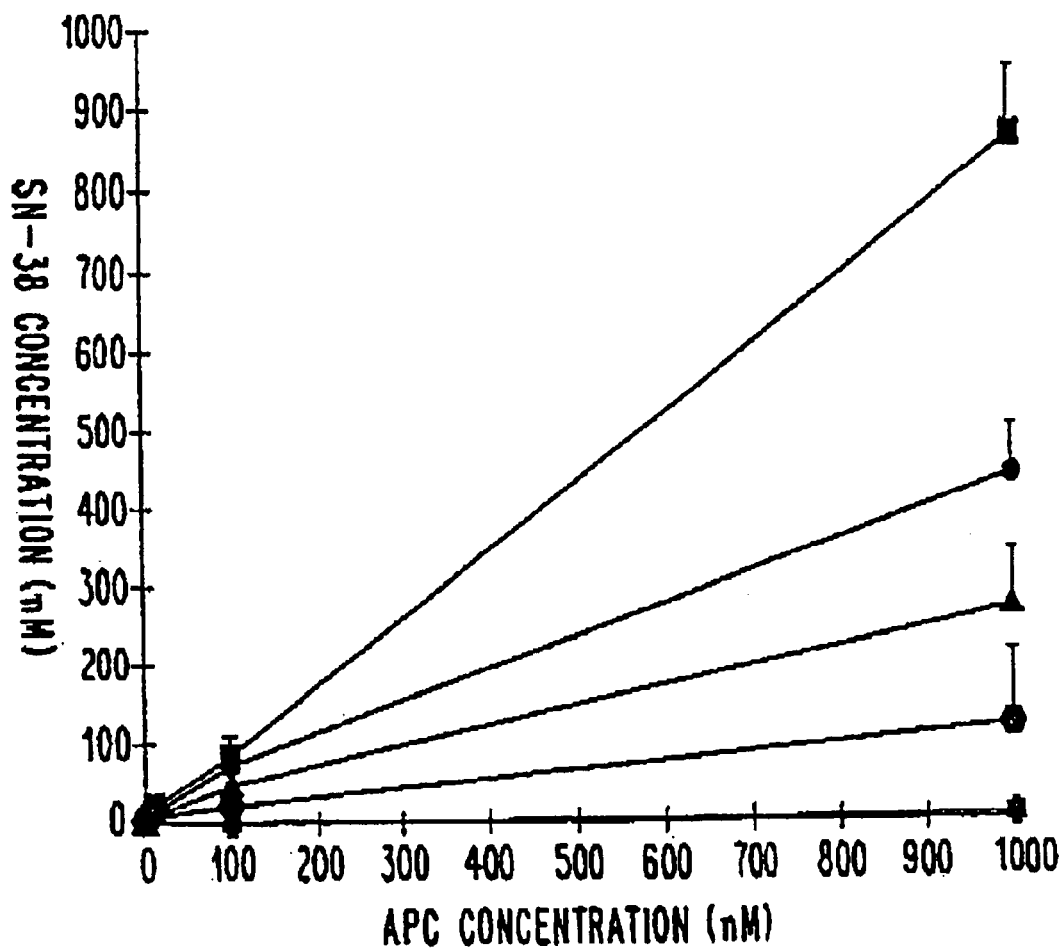

FIG. 6 is a linegraph showing the conversion of APC, depicted on the X-axis at nanomolar concentrations, to SN-38, depicted on the Y-axis at nanomolar concentrations, in vitro by the activity of rabbit liver CE given at doses of 0 (filled cross), 10 (filled hexagon), 25 (filled triangle), 50 (filled circle) or 100 (filled square) units. Data presented represent the mean response at each dose level.

Figure 7:
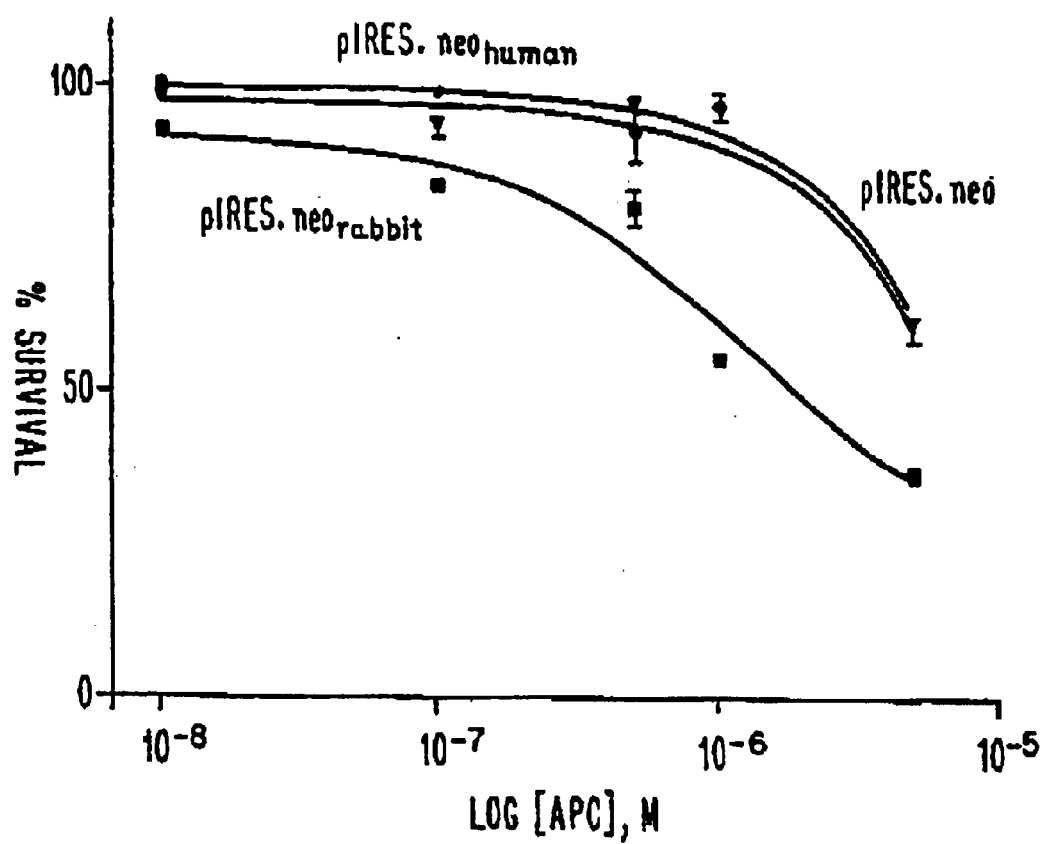

FIG. 7 is a linegraph showing a comparison of the sensitization, depicted as t survival on the Y-axis, of U-373 glioma cells exposed to APC, depicted as log [APC] at concentrations from $10^{-8}$ to $10^{-5}$ M on the X-axis, from in situ expression of rabbit liver CE (filled squares) and human alveolar macrophage CE (filled circles). Cells were exposed for 2 hours to APC.

FIG. 8 provides the chemical structures of CPT-11, APC and SN-38.

Figure 9A:
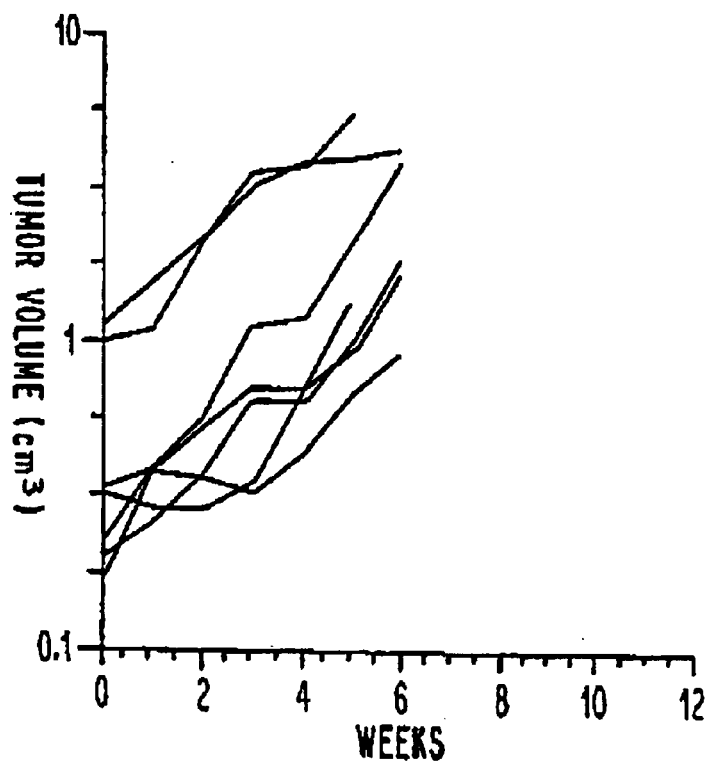
Figure 9B:
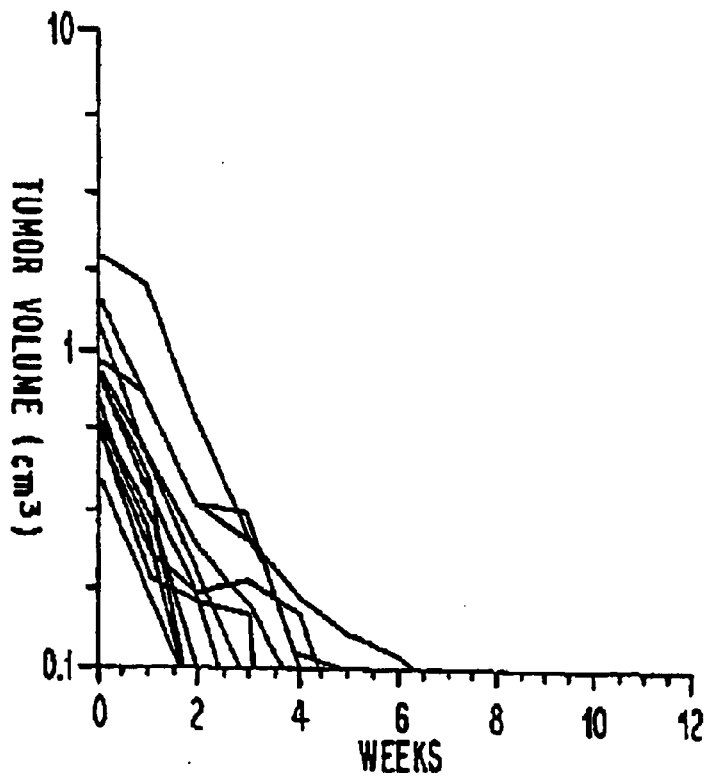
Figure 9C:
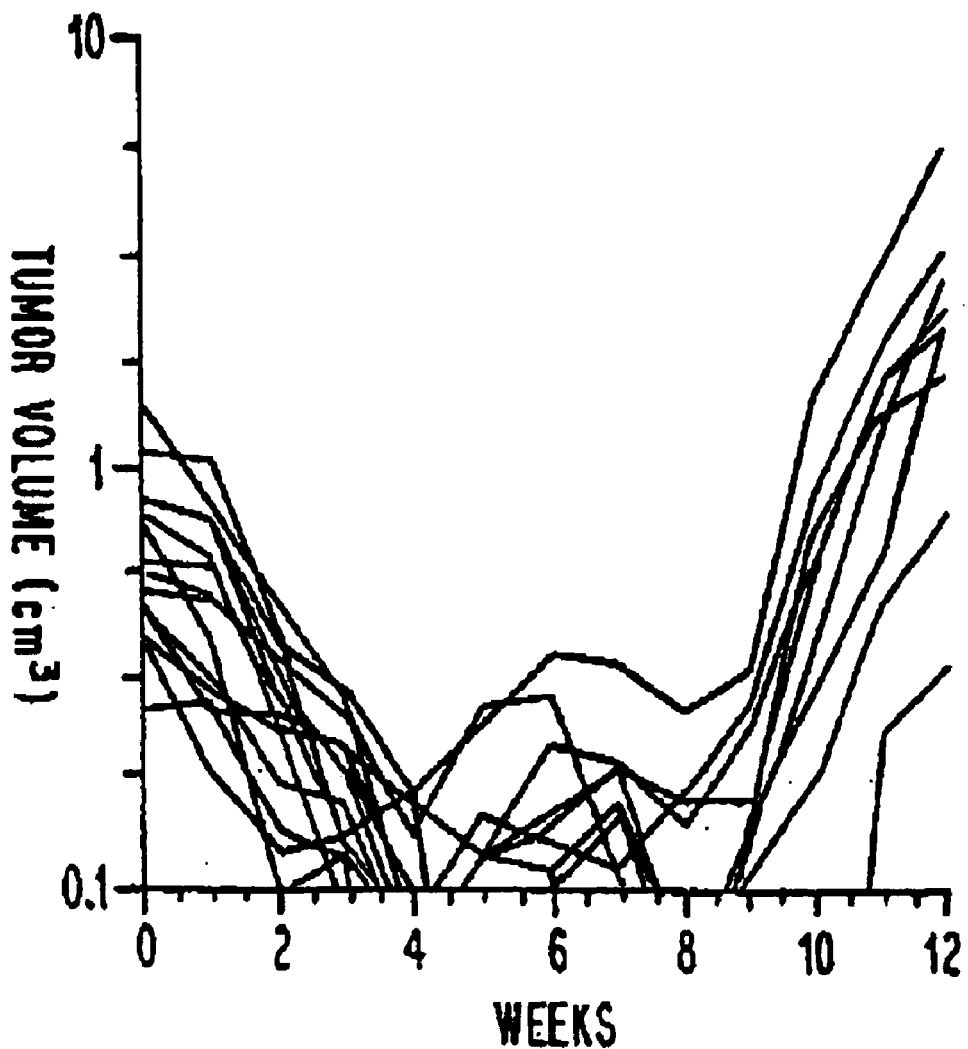

FIGS. 9A, 9B, and 9C are linegraphs showing the responses of mice bearing Rh30 and Rh30pIRES$_{rabbit}$ rhabdosarcoma xenografts to CPT-11 treatment. Each line on each graph shows the growth of an individual tumor. The tumor growth rate is depicted on the Y-axis of each graph in terms of tumor volume and is plotted as a function of time in weeks (X-axis). FIG. 9A depicts cells expressing rabbit CE (Rh30pIRES$_{rabbit}$) not treated with CPT-11. FIG. 9B depicts cells expressing rabbit CE (Rh30pIRES$_{rabbit}$) and then treated with CPT-11 and shows complete tumor regression, even out to 12 weeks. FIG. 9C depicts control cells (Rh30) exposed to CPT-11 and shows initial regression but regrowth.

Figure 10:
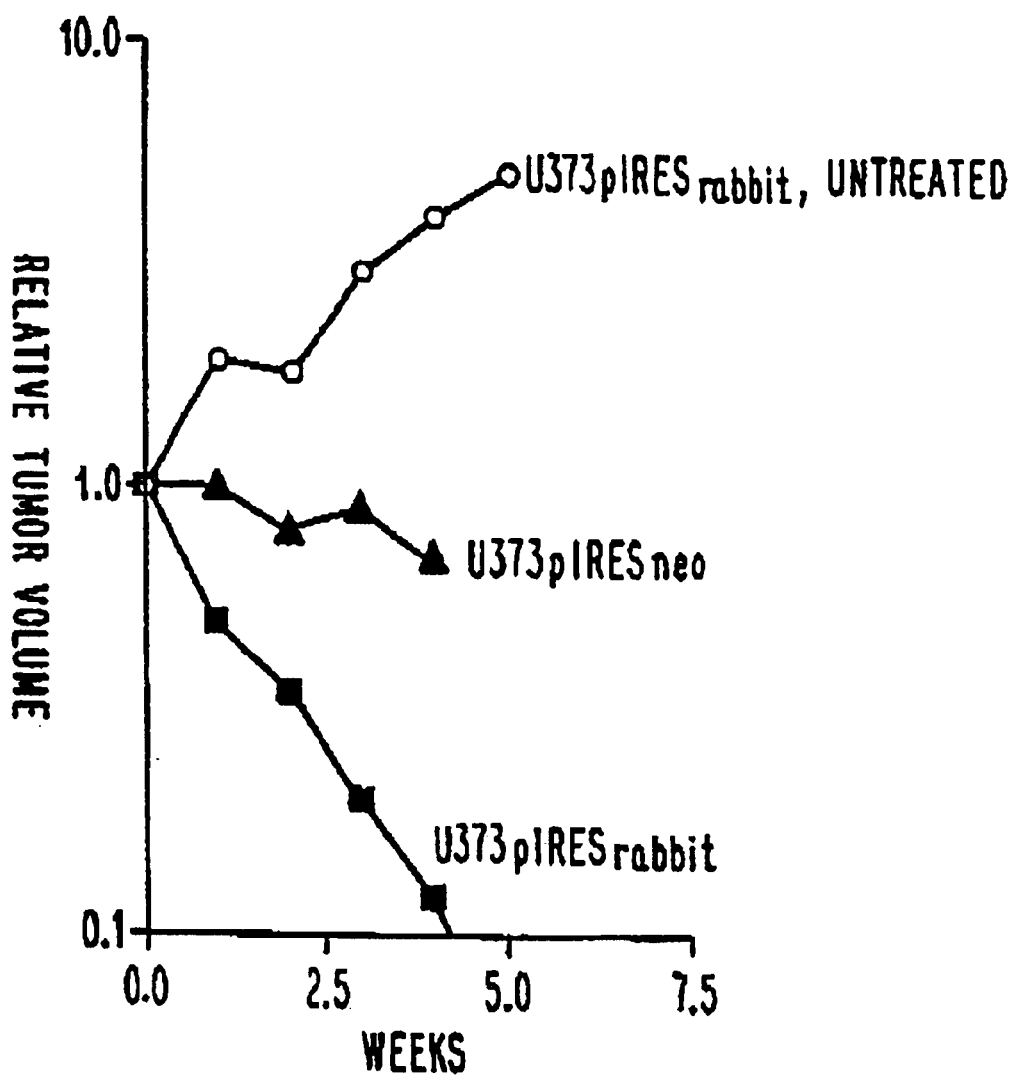

FIG. 10 is a linegraph showing the effects of CPT-11 treatment on U373 glioblastoma xenografts expressing rabbit CE. Mice bearing xenografts were treated with CPT-11 (7.5 mg/kg for 5 days) for three treatment cycles. The tumor growth rate is depicted on the Y-axis in terms of tumor volume and is plotted as a function of time in weeks (X-axis). Open circles depict the tumor volume of untreated U373 xenografts expressing rabbit CE. Filled triangles depict the response of control xenografts (no rabbit CE) treated with CPT-11. Filled squares depict the response of cells expressing rabbit CE and treated with CPT-11. The data show that tumor regression was seen only in treated cells expressing rabbit CE. Each point represents the mean of 14 tumors in 7 individual mice.

Figure 11:
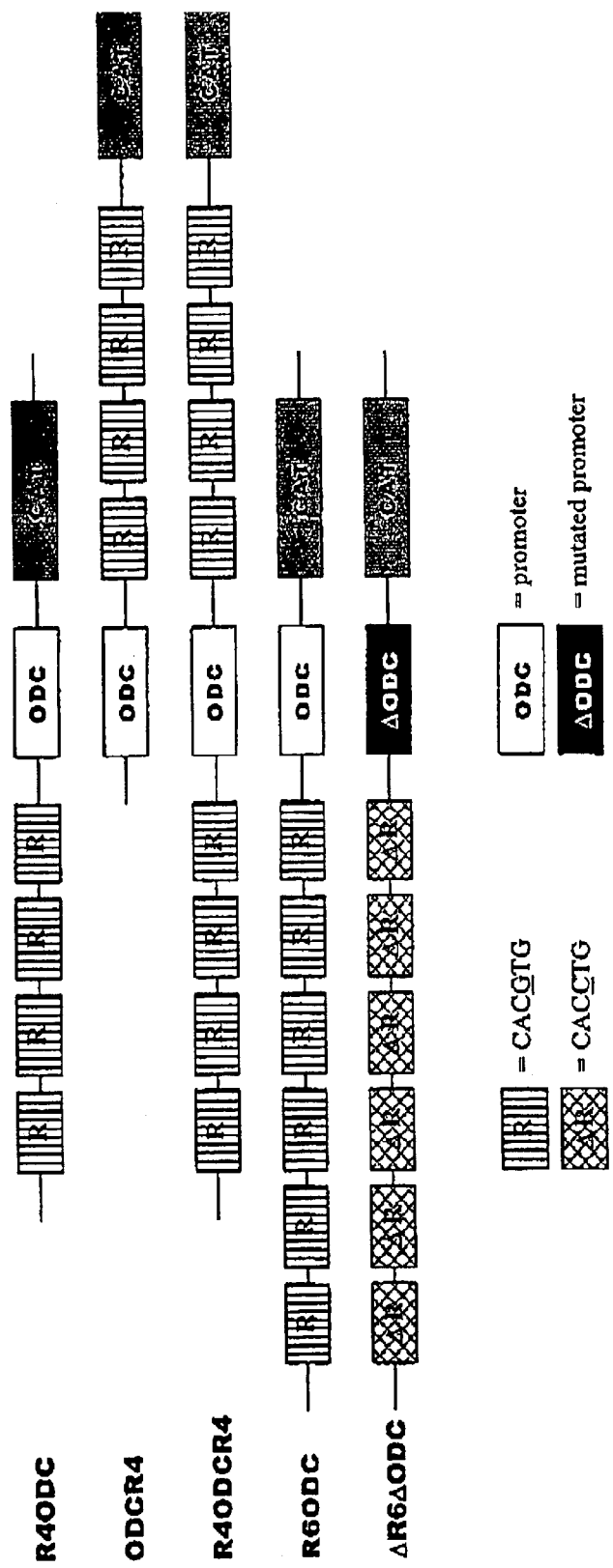

FIG. 11 depicts the modifications of the myc-responsive ornithine decarboxylase promoter where ODC is the ornithine decarboxylase promoter, R4 and R6 are 4 repeats and 6 repeats, respectively, of the myc-responsive CACGTG E-box sequence, ΔR6 and ΔODC are constructs analogous to R6 and ODC, respectively, except the E-box sequence has been changed to CACCTG, and CAT is the chloramphenicol acetyltransferase gene.

DETAILED DESCRIPTION OF THE INVENTION

CPT-11 is a promising anti-cancer prodrug, that when given to patients, is converted to its active metabolite SN-38 by a human carboxylesterase. However, conversion in patients is relatively inefficient and less than 5% of the prodrug is metabolized to SN-38 (Rivory, L. P. et al. 1997. *Clin. Cancer Res.* 3:1261–1266). In patients, this prodrug is also metabolized to APC (Haaz, M-C. et al. 1998. *Cancer Res.* 58:468–472). APC has little, if any, active anti-tumor activity and is not converted to an active metabolite in humans (Rivory, L. P. et al. 1996. *Cancer Res.* 56:3689–3694). Accordingly, high concentrations of this prodrug must be administered to achieve effective levels of active drug in vivo. However, myelosuppression and secretory diarrhea limit the amount of prodrug that can be administered to patients.

In the present invention, a method of sensitizing tumor cells to reduce the effective dose of a prodrug required to inhibit tumor cell growth is provided which comprises transfecting selected tumor cells with a polynucleotide under the control of a disease-specific responsive promoter such as a myc promoter. The present invention exploits the tumor-specific overexpression of oncogenes of the myc family to produce selective killing with a chemotherapeutic prodrug.

In accordance with one aspect of the present invention there are provided polynucleotides which encode carboxy-lesterases capable of metabolizing a chemotherapeutic prodrug and inactive metabolites thereof to active drug. By "polynucleotides" it is meant to include any form of DNA or RNA such as cDNA or genomic DNA or MRNA, respectively, encoding these enzymes or an active fragment thereof which are obtained by cloning or produced synthetically by well known chemical techniques. DNA may be double- or single-stranded. Single-stranded DNA may comprise the coding or sense strand or the non-coding or antisense strand. Thus, the term polynucleotide also includes polynucleotides which hybridize under stringent conditions to the above-described polynucleotides. As used herein, the term "stringent conditions" means at least 60% homology at hybridization conditions of 60° C. at 2×SSC buffer. In one embodiment, the polynucleotide comprises the cDNA depicted in FIG. 4 (SEQ ID NO:20) or a homologous sequence or fragment thereof which encodes a polypeptide having similar activity to that of this rabbit liver CE enzyme. In another embodiment, the polynucleotide comprises a cDNA as depicted in SEQ ID NO:27 encoding human intestinal carboxylase as depicted in SEQ ID NO:28. Due to the degeneracy of the genetic code, polynucleotides of the present invention may also comprise other nucleic acid sequences encoding these enzymes and derivatives, variants or active fragments thereof. The present invention also relates to variants of these polynucleotides which may be naturally occurring, i.e., allelic variants, or mutants prepared by well known mutagenesis techniques.

Also provided in the present invention are vectors comprising polynucleotides of the present invention and host cells which are genetically engineered with vectors of the present invention to produce CE or active fragments of this enzyme. Generally, any vector suitable to maintain, propagate or express polynucleotides to produce the enzyme in the host cell may be used for expression in this regard. In accordance with this aspect of the invention the vector may be, for example, a plasmid vector, a single- or double-stranded phage vector, or a single- or double-stranded RNA or DNA viral vector. Such vectors include, but are not limited to, chromosomal, episomal and virus-derived vectors e.g., vectors derived from bacterial plasmids, bacteriophages, yeast episomes, yeast chromosomal elements, and viruses such as baculoviruses, papova viruses, SV40, vaccinia viruses, adenoviruses, fowl pox viruses, pseudorabies viruses and retroviruses, and vectors derived from combinations thereof, such as those derived from plasmid and bacteriophage genetic elements, cosmids and phagemids. Selection of an appropriate promoter to direct mRNA transcription and construction of expression vectors are well known. In general, however, expression constructs will contain sites for transcription initiation and termination, and, in the transcribed region, a ribosome binding site for translation. The coding portion of the mature transcripts expressed by the constructs will include a translation initiating codon at the beginning and a termination codon appropriately positioned at the end of the polypeptide to be translated. Examples of eukaryotic promoters routinely used in expression vectors include, but are not limited to, the CMV immediate early promoter, the HSV thymidine kinase promoter, the early and late SV40 promoters, the promoters of retroviral LTRs, such as those of the Rous Sarcoma Virus(RSV), and metallothionein promoters, such as the mouse metallothionein-I promoter. Vectors comprising the polynucleotides can be introduced into host cells using any number of well known techniques including infection, transduction, transfection, transvection and transformation. The polynucleotides may be introduced into a host alone or with additional polynucleotides encoding, for example, a selectable marker. Host cells for the various expression constructs are well known, and those of skill can routinely select a host cell for expressing the rabbit liver CE enzyme or the human intestinal CE enzyme in accordance with this aspect of the present invention. Examples of mammalian expression systems useful in the present invention include, but are not limited to, the C127, 3T3, CHO, HeLa, human kidney 293 and BHK cell lines, and the COS-7 line of monkey kidney fibroblasts. Alternatively, as exemplified herein, rabbit CE can be expressed in *Spodoptera frugiperda* Sf21 cells via a baculovirus vector (see Example 3).

The present invention also relates to compositions comprising a polynucleotide of the present invention which have been found to be useful in sensitizing tumor cells to CPT-11 cytotoxicity by combination therapy of the prodrug and a CE enzyme. The present invention thus provides methods for sensitizing tumor cells to a prodrug oncologic agent. In this context, by "sensitizing" it is meant that the effective dose of the prodrug can be reduced when the compositions and methods of the present invention are employed. In a case where the prodrug's therapeutic activity is limited by the occurrence of significant toxicities, or dose-limiting toxicities, sensitization of tumor cells to the prodrug is especially useful.

In one embodiment, selected tumor cells are transfected with the cDNA of the present invention and expressed via a well known promoter such as the CMV promoter or, more preferably, via a disease-specific responsive promoter which specifically targets the selected tumor cells. Targeted gene expression in tumor cells has been achieved using disease-specific responsive promoters such as carcinoembryonic antigen, HER-2/neu, Myc-Max response elements, and DF3/MUC. Thus, a composition comprising the cDNA rabbit liver CE or human intestinal CE and a disease-specific responsive promoter such as these can be used to transfect and sensitize tumor cells containing the disease-specific responsive promoter. Accordingly, the present invention provides a means for exploiting tumor-specific expression associated with a disease-specific responsive promoter to provide for selective therapy of tumors.

Since myc expression is deregulated in a wide variety of human tumors, myc is an attractive target for chemotherapeutics. No known drug specifically interacts with either the c-myc or N-myc protein. However, cells overexpressing a myc oncogene can be targeted with compositions of the present invention comprising a polynucleotide of the present invention under the control of a myc specific promoter. Thus, using the present invention the tumor-specific over-expression of c-myc and N-myc can be exploited to produce selective killing with a chemotherapeutic agent. Specifically, transcription of genes under the control of the promoter containing the CACGTG (SEQ ID NO:22) binding sequence of either N-myc or c-myc are upregulated in cells overexpressing these myc genes, producing tumor cell-specific expression of the polynucleotide encoding the CE that is capable of activating the chemotherapeutic prodrug CPT-11.

The ability of a promoter to regulate gene expression was confirmed in cell lines overexpressing c-myc, SJ-G2 and NCI-H82 cells (which overexpress c-myc) and Rh28 cells (which have no detectable levels of c-myc protein). In these experiments, cells were transiently transfected with a plasmid containing the ODC promoter controlling expression of a reporter gene for chloramphenicol acetyltransferase. A mutated ODC promoter in which c-myc transactivation domains have been inactivated by point mutations was used as a control. A 4- to 5-fold increase in reporter activity was observed in SJ-G2 cells and NCI-H82 cells, respectively, following transfection with the plasmid containing native ODC promoter as compared to the mutant promoter sequence. No significant increase in promoter activity was observed in Rh28 cells. These results are consistent with c-myc-mediated activation of transcription by binding to the cognate sequence within the ODC promoter. In addition, the levels of activation were similar to that seen with reporter constructs when enforced co-expression of c-myc occurs during transfection of CV-1 and NIH-3T3 cells.

Additional experiments were conducted to identify disease-specific responsive promoters for c-myc and n-myc expressing cell lines with optimal activity. The strategy used in these experiments was to combine a myc-specific promoter with a myc-responsive enhancer. A similar combination approach with a PSA promoter and enhancer was shown to result in production of a strong, specific promoter/enhancer for prostate cancer cells (Pang, S. et al. 1995. *Human Gene Therapy* 6:1417–1426; Pang, S. et al. 1997. *Cancer res.* 57:495–499). Specifically, modified ornithine decarboxylase (ODC) promoters were constructed (FIG. 11). The endogenous ODC promoter contains two CACGTG E-box sequences. The modified ODC promoters of the present invention were constructed by inclusion of additional CACGTG E-box sequences as follows: the promoter referred to herein as R4ODC comprised 4 additional CACGTG E-box sequences 5' to the endogenous promoter; the promoter referred to herein as ODCR4 comprised 4 additional CACGTG E-box sequences 3' to the endogenous promoter; the promoter referred to herein as R4ODCR4 comprised 4 additional CACGTG E-box sequences 5' as well as 3' to the ODC promoter; and the promoter referred to herein R6ODC comprised 6 additional CACGTG E-box sequences 5' to the promoter. Accordingly, the constructs contained a total of 6, 6, 10 and 8 CACGTG sites, respectively. Mutated ODC promoters were constructed that encoded a mutated ODC promoter (ΔODC) with a mutated E-box sequence of CACCTG (SEQ ID NO:25). The promoter referred to herein as LR6ODC had 6 additional mutated E-box sequences 5' to ΔODC. The negative control ΔR6ΔODC promoter construct contained a total of 8 modified E-box sequences. All constructs further comprised the chloramphenicol acetyltransferase (CAT) gene.

The relative transcriptional efficiency of the promoter/enhancer constructs was evaluated in the c-myc expressing glioblastoma cell line SJ-G2. The negative control in these experiments was the SJ-G3 cell line. Immunoblots showed that the 64 kDa form of c-myc protein was readily detectable in SJ-G2 glioblastoma cells, but not in SJ-G3 glioblastoma cells. Neither cell line expressed the 67 kDa form of c-myc, as has been reported for other tumor cells and cell lines.

To assess the ability of endogenous c-myc to activate the promoter/enhancer constructs shown in FIG. 11, each construct was ligated into the pCAT3Basic vector and aliquots of SJ-G2 cells were transiently transfected with each of the plasmids. Results were reported as CAT activity normalized to β-galactosidase activity, with activity produced by the unmodified ODC promoter sequence arbitrarily set equal to 1.0.

The endogenous ODC promoter increased CAT activity ~3-fold relative to controls with no ODC promoter. Four additional CACGTG E box sequences 5' to the endogenous ODC promoter (R4ODC) increased promoter activity 7.2-fold relative to the unmodified promoter. Four additional CACGTG E box sequences 3' to the ODC promoter or both 5' and 3' to the endogenous promoter produced CAT activity similar to the unmodified promoter. The highest level of CAT activity, 14-fold greater than the ODC promoter, ~50-fold compared to promoterless controls, was produced by constructs containing six additional CACGTG E box sequences 5' to the ODC promoter (R6ODC). The negative control comprising the ΔR6ΔODC sequence gave results equivalent to controls lacking a promoter. SJ-G3 cells, which do not have immunodetectable c-myc, expressed only background levels of CAT activity when transfected with plasmids that contained either the most efficient R6ODC sequence or the ΔR6ΔODC negative control sequence. These data demonstrate that the R6ODC enhancer/promoter is the most efficient of the constructs tested in regulating expression of a reporter enzyme in the SJ-G2 glioblastoma cell line that overexpresses c-myc. Accordingly, this promoter is particularly useful in the present invention in expression vectors for carboxylesterases.

The cDNA of rabbit liver CE was isolated by synthesizing degenerate oligonucleotides from amino acid residues 1–5 (SEQ ID NO:6) and 518–524 (SEQ ID NO:10) of a published rabbit CE protein sequence (Korza, G. and J. Ozols. 1988. *J. Biol. Chem.* 263:3486–3495). The oligonucleotides constructed are shown in FIG. 2. To amplify the rabbit cDNA by PCR, cDNA was prepared from rabbit liver poly A+ mRNA and multiple samples were prepared that contained the combination of oligonucleotide primers. Using PCR techniques, a single product was obtained from one set of reactions that upon DNA sequencing was shown to encode the rabbit CE.

Since this represented a partial cDNA, both 5' and 3' RACE were used to amplify the entire coding sequence. Unique primers were designed from the partial DNA sequence. These oligonucleotides were used in combination with the AP1 primer to amplify sequences prepared from Marathon adapted rabbit liver CDNA. Touchdown PCR (Don, R. H. et al. 1991. *Nucleic Acids Res.* 19:4008) was performed in accordance with the Marathon cDNA amplification protocol.

The complete sequence of the CDNA (SEQ ID NO:20) and the derived amino acid sequence (SEQ ID NO:21) of a rabbit liver CE are shown in FIG. 4. Northern analysis of the poly A+ mRNA from the rabbit liver with a [$^{32}$P]-labeled cDNA confirmed the presence of a single transcript of approximately 1.84 knt. No cross reaction was observed with any other MRNA, consistent with this cDNA representing a unique RNA species.

Further, comparison of the amino acid sequence of the polypeptide encoded by the cDNA of the present invention with the published amino acid sequence for rabbit CE (Swissprot Accession Number P12337; Korza, G. and J. Ozols. 1988. *J. Biol. Chem.* 263:3486–3495) showed three mismatches. In addition, the polypeptide encoded by the cDNA of the present invention contains an 8 amino acid insert and an 18 amino acid leader sequence at the N-terminus which the published sequence does not contain. Accordingly, another aspect of the present invention relates to novel polypeptides encoded by polynucleotides of the present invention. By "polypeptide" it is meant to include the amino acid sequence of SEQ ID NO: 21 depicted in FIG. 4 and fragments, derivatives and analogs which retain essentially the same biological activity and/or function as this rabbit liver CE.

The rabbit cDNA was expressed in bacteria. The 1.7 kb cDNA was ligated into pET32b and transformed into *E. coli* L21(DE3). Two clones were isolated containing the rabbit cDNA either in the correct (pETRABFL) or incorrect (pETLFBAR) orientation with respect to the T7 promoter. Following induction of expression in liquid culture with IPTG, cell extracts were analyzed by SDS-PAGE and Western blotting. A 75 kDa protein resulted from the fusion of the rabbit CE with the thioredoxin protein in pETRABFL. Western analysis with the rat liver microsomal CE antibody and horseradish peroxidase (HRP)-conjugated protein S confirmed that the 75 kDa protein encoded by PETRABFL contained the rabbit CE. Since other CEs are located in the ER and the primary sequence of the rabbit enzyme contains similar characteristic leader and anchor sequences (Satoh, T. and M. Hosokawa. 1995. *Toxicol. Lett.* 82/83:439–445), it is likely that the compartmentalization of the CE to the ER is required for enzymatic activity. Indeed, overexpression of the human alveolar macrophage CE in *E. coli* failed to generate CE activity, however transfection of mammalian cells with the same cDNA yielded significant conversion of o-NPA by whole cell extracts. In addition, the rabbit CE demonstrated greater than 85% homology with human alveolar macrophage CE yet the latter enzyme failed to convert CPT-11 to SN-38 in mammalian cells. This indicates that while CEs may have a broad range of substrate specificities, the efficiency with which similar enzymes within different species can utilize a particular substrate varies dramatically.

To confirm that the cDNA encoded CE, the 1.7 kb EcoRI fragment was ligated into pCIneo to generate pCIRABFL and the plasmid transiently transfected into Cos7 cells. pCIneo contains the SV40 origin of replication allowing plasmid amplification in cells expressing the large T antigen, such as Cos7. The IC$_{50}$ value for CPT-11 for cells expressing the CE was approximately 8–80 fold, and most typically about 56 fold, less than that of the parent cell line thus indicating that the enzyme has sensitized mammalian cells to CPT-11 (see FIG. 5).

Rabbit CE has also been expressed in *Spodoptera frugiperda* S21 cells via a baculovirus vector. CE secreted in these cells was concentrated by ultrafiltration to approximately 1 ml containing approximately 30,000 micromoles/ millimeter of enzyme activity.

Experiments were also performed to determine whether human CE from sources other than liver were capable of converting CPT-11 to its active metabolite. Mouse small intestine is known to express high levels of CE that can convert CPT-11 to SN-38. Accordingly, the ability of human intestinal CE (hiCE) as an activator of CPT-11 was examined. Using human intestinal mucosal biopsy tissue, the conversion of o-NPA to nitrophenol by whole tissue sonicates was monitored. CE activity was identified in both small intestine and colon samples, with activity levels in small intestine being much less than the levels seen with human liver. However, the amount of CPT-11 conversion was essentially the same on a mg protein basis (Table 1). Thus, these data indicate that for the total levels of esterases present in tissue, the percentage of CPT-11 converting enzymes in the small intestine is greater than the percentage in the liver.

TABLE 1

Metabolism of o-NPA and CPT-11 by Human Biopsy Extracts

| Sample | o-NPA Conversion (μmoles/min/mg) | CPT-11 Conversion (pmoles/hr/mg) |
|---|---|---|
| Small intestine | 113.0 ± 9.2 | 7.57 |
| Small intestine | 67.6 ± 4.1 | 3.13 |
| Small intestine | 61.0 ± 2.0 | 3.83 |
| Colon | 75.9 ± 2.6 | 1.34 |
| Colon | 46.5 ± 1.2 | 0.65 |
| Colon | 86.3 ± 5.2 | 2.06 |
| Liver | 1928.9 ± 251.0 | 7.15 |
| Liver | 802.7 ± 68.2 | 2.72 |

A cDNA encoding a human intestinal CE has been isolated (Schwer et al. 1997 Biochem. Biophys. Res. Commun. 233(1):117–120) and shown to be predominately expressed in the small intestine. To determine whether the isolated enzyme was capable of activation of CPT-11, the full length coding sequence of the human intestinal CE (GenBank Accession No. Y09616) was obtained by PCR using oligonucleotide primers that created XbaI restriction sites adjacent to the ATG initiation and TAG termination codons. The cDNA (SEQ ID NO:27) was amplified from human liver cDNA (Clontech, Palo Alto, Calif.) using Taq polymerase. Products were then ligated into pCR-II TOPO and sequenced to verify their identity. One clone containing the bona fide sequence was ligated into pCEneo (pClhiCE) for expression in mammalian cells. Sequence analysis indicated that the rabbit CE demonstrates 81% identity with human liver CE but only 47% identity with hiCE. In addition, human liver CE demonstrated 49% identity with hiCE.

Accordingly, sequence similarity does not predict the ability of a CE enzyme to metabolize CPT-11. Instead, computer modeling studies indicate the ability of a CE to activate CPT-11 is dependent on the residues that form the entrance to the active site gorge of these proteins. Thus, it is expected that other CEs with residues similar to those forming the entrance to the active site gorge in rabbit liver CE and human intestinal CE will also be useful in metabolizing chemotherapeutic prodrugs and inactive metabolites thereof, such as CPT-11 and APC, respectively, to active drug.

Using sonicates of cells expressing hiCE, experiments showed that there was efficient conversion of both o-NPA and CPT-11. No CE activity or CPT-11 conversion was detected in media of cells transfected with hiCE indicating that the protein was not secreted from cells (Table 2).

TABLE 2

Conversion of o-NPA and CPT-11 by COS-7 Cells

| Plasmid | Enzyme | o-NPA Conversion (μmoles/min/mg) | CPT-11 Conversion (pmoles/hr/mg) |
|---|---|---|---|
| pCIneo | none | 6.7 ± 0.15 | 3.4 |
| pCIneo[1] | media | 13.3 ± 2.7 | 0.9 |
| pClhiCE | hiCE | 1735.6 ± 163.1 | 654.3 |
| pClhiCE[1] | media | 30.9 ± 2.8 | 2.1 |
| pCIHUMCAR | hCE1 | 4780.3 ± 279.8 | 9.6 |
| pCIRAB | rabbit | 2755.5 ± 271.2 | 2323.0 |

Another aspect of the present invention relates to the ability of compositions comprising a polynucleotide encoding a carboxylesterase and a disease-specific responsive promoter of selected tumor cells to sensitize the tumor cells to a chemotherapeutic prodrug. The ability of a rabbit CE or a human intestinal CE of the present invention to sensitize human tumor cells to CPT-11 was examined. Experiments were first performed to confirm that the metabolite produced by the activity of a CE of the present invention is biologically active in vitro. Rh30 cells were exposed to the products of each reaction for one hour and the percentage of growth inhibition was determined. As expected, Rh31 cells exposed to 1 to 5 units of CE that had been inactivated by heating produced no inhibition of cell growth. In contrast, reaction products of CPT-11 incubated with 1 to 5 units of active CE produced a 30–60% inhibition of cell growth. These data are consistent with the conversion of CPT-11 to SN-38 by CE in these cells. Similar confirmatory experiments were performed with COS-7 cells.

The CE activity of extracts of the transfected cells was then determined. First, the $IC_{50}$ values for CPT-11 in Rh30 rhabdomyosarcoma cells that had been stably transfected with a rabbit liver CE cDNA of the present invention or the pIRES vector alone were also determined. Cells transfected with the CE CDNA contained approximately 60-fold more CE activity than control cells. The $IC_{50}$ of CPT-11 for Rh30pIRES cells (no CE cDNA) was $4.33 \times 10^{-6}$ M while the $IC_{50}$ for the Rh30pIRES$_{rabbit}$ cells was $5.76 \times 10^{-7}$ M. Therefore, the transfected cells were more than 8-fold more sensitive to CPT-11. These data are consistent with an increased conversion of CPT-11 to SN-38 in the cells transfected with a CE of the present invention.

To determine whether the human intestinal CE could confer similar sensitivity to CPT-11, the effect of the drug on growth of COS-7 cells expressing hiCE was examined. The $IC_{50}$ of cells expressing hiCE was 0.5 μM, approximately 11-fold less than that of cells transfected with the parent plasmid (pCEneo $IC_{50}$=5.4 μM). These data indicate that efficient in vivo activation of CPT-11 by hiCE also occurred leading to a sensitization of cells to the drug.

Experiments have also been conducted which demonstrate that a CE of the present invention is capable of converting the inactive metabolite APC to SN-38. Structures of these compounds are shown in FIG. 8. FIG. 6 shows the results of experiments in vitro where APC is converted to SN-38 in a concentration-dependent manner by a rabbit CE of the present invention. These data confirm the unique ability of a CE of the present invention to activate the prodrug CPT-11, as well as to activate one of its metabolites. Further, experiments in U-373 cells that express a CE of the present invention showed that these cells were sensitized to the growth inhibitory effects of APC (see FIG. 7).

In vivo efficacy of the CE of the present invention to sensitize tumor cells to CPT-11 has also been demonstrated in two different types of tumor cells. Experiments conducted in a mouse model demonstrate that a CE of the present invention is capable of sensitizing cells to the growth inhibitory effects of CPT-11.

In a first set of experiments, the ability of rabbit CE to sensitize Rh30 rhabdomyosarcoma human tumor cells grown as xenografts in immune-deprived mice was demonstrated. In this preclinical model, expression of the transfected cDNA for rabbit CE was maintained for at least 12 weeks. Importantly, tumors were advanced (greater than 1 cm³ in volume) before treatment with CPT-11 began. As depicted in FIG. 9B, tumors in mice expressing CE and treated with 2.5 mg CPT-11/kg/day for five days each week for two weeks (one cycle of therapy), repeated every 21 days for a total of three cycles (over 8 weeks), regressed completely and did not regrow during the 12 weeks of the study. In contrast, tumors that did not express the CE regressed only transiently with CPT-11 treatment, with regrowth occurring within one week after CPT-11 treatment stopped (see FIG. 9C).

In a second set of experiments, human U373 glioblastoma xenografts that express rabbit liver CE were shown to be more sensitive to CPT-11 than xenografts transfected with a control plasmid (no rabbit CE). Xenografts established from cells transfected with the plasmid encoding rabbit CE regressed completely while xenografts from cells transfected with the control plasmid showed stable disease but no significant regression (see FIG. 10).

Thus, these data support the use of the combination of polynucleotide encoding a CE of the present invention and CPT-11 to reduce the amount of CPT-11 needed to produce inhibition of tumor cell growth, or to sensitize the tumor cells to CPT-11. These data also support the use of the present invention to allow for decreased dosage with CPT-11 in cancer patients, thus reducing the likelihood of dose-limiting toxicity. Further, as shown by these experiments, APC, which is relatively nontoxic, can also be used as a chemotherapeutic prodrug in combination with a CE of the present invention to produce tumor-specific cell death while minimizing toxic side effects.

The present invention thus also relates to a method for treating cancer with reduced side effects. In one embodiment, a polynucleotide of the present invention is inserted into a viral vector using a gene transfer procedure. Preferred viral vectors include, but are not limited to, retroviral, adenoviral, herpesvirus, vaccinia viral and adeno-associated viral vectors. In this embodiment, it is preferred that the vector further comprise a disease-specific responsive promoter. The vectors can then be injected into the site of tumor removal along with systemic administration of a prodrug such as CPT-11 to inhibit the recurrence of tumors due to residual tumor cells present after surgical resection of a tumor.

Alternatively, the viral vector can be used to purge bone marrow of contaminating tumor cells during autologous transplant. Bone marrow purging via a viral vector such as adenovirus which expresses a CE of the present invention is performed ex vivo. Efficiency of removal of contaminating tumor cells is determined by PCR assays of purged samples. Data indicate that the method of the present invention is applicable to an animal model for purging bone marrow of neuroblastoma cells such as that described in Example 6. Methods for preparation of the vectors, modes of administration, and appropriate doses of prodrug are well known to those of skill in the art. Other methods of gene delivery such as chemical and liposome-mediated gene transfer, receptor-mediated DNA uptake, and physical transfer by gene guns or electroporation may also be employed.

Another method for delivering CEs to selected tumor cells involves antibody direct enzyme prodrug therapy (ADEPT). In this method, human tumors are targeted by conjugation of tumor-specific marker antibody with a molecule such as rabbit liver CE. Cellular internalization of the complex and release of active CE would be achieved, leading to CPT-11 activation that is specific for cells expressing the marker antigen. Since the array of marker molecules expressed upon the cell surface is different for each tumor type, markers specific for each targeted tumor type can be selected as appropriate. Similarly, the use of avidin-biotin conjugated molecules to target tumor cells (Moro, M. et al. 1997. *Cancer Res.* 57:1922–1928) is also applicable for localization of CEs to the cell surface followed by drug activation at the targeted cell.

The rabbit liver CE is localized in the endoplasmic reticulum. Removal of the six terminal amino acids results in secretion of active protein into the extracellular milieu. Both the secreted and the endoplasmic reticulum-localized protein can convert CPT-11 to SN-38; therefore, the potential exists for a bystander effect from cells expressing the secreted enzyme. A similar bystander effect has been demonstrated for other enzyme/prodrug combinations, such as HSVtk and ganciclovir (Dilber, M. S. et al. 1997. *Cancer Res.* 57:1523–1528), and results in increased cytotoxicity. Extracellular activation of CPT-11 may result in more efficient eradication of MRD in that uninfected neighboring tumor cells would be killed by exogenously produced SN-38. Gene therapy protocols with a secreted CE in combination with CPT-11 may therefore be more appropriate for the elimination of residual tumor tissue. Accordingly, in this embodiment, it may be preferred to use a fragment of a polynucleotide encoding a polypeptide which is secreted. For example, for rabbit liver, a cDNA encoding a protein which does not contain the six terminal amino acids depicted in FIG. 4, or a cDNA encoding a rabbit liver CE enzyme consisting of amino acids 1–543 (SEQ ID NO:26) of FIG. 4, may be preferred. Additionally, recent reports indicate that the tethering of drug activating enzymes to the extracellular cell surface can result in anti-tumor activity in human tumor xenografts when combined with appropriate prodrug (Marais, R. et al. 1997. *Nature Biotech.* 15:1373–1377). A tethered enzyme generates a local bystander effect since the protein is not free to circulate in the plasma. Attachment of a CE of the present invention to the cell surface should result in local extracellular activation of CPT-11 to SN-38 and enhance local cell kill. Purging bone marrow of contaminating tumor cells will be accomplished by an intracellular enzyme, whereas eradication of MRD is better achieved by an enzyme that activates CPT-11 at an extracellular location.

CEs of the present invention cleave the COOC bond present as an ester linkage in CPT-11 to generate SN-38 (see FIG. 8). Since these enzymes may also catalyze the activation of other compounds that contain such a linkage, the present invention also provides assays for screening for compounds that contain this and related moieties. In one embodiment, the assay of the present invention is conducted in a cell system using, for example, yeast, baculovirus, or human tumor cell lines. In this embodiment, compounds activated by CE will be identified and assessed for anticancer activity by growth inhibition or clonogenic cell survival assays using cells expressing or lacking a CE of the present invention. Alternatively, compounds can be screened in cell-free assays using a CE of the present invention isolated from host cells expressing this enzyme. In this embodiment, the ability of the enzyme to cleave a COOC ester linkage of a candidate compound is measured directly in a standard enzyme assay buffer system containing a CE of the present invention. Known concentrations of candidate compounds can be added to assay tubes containing a biological buffer such as HEPES at pH 7.4 and the enzyme, and incubated at 37° C. for a selected amount of time. The reaction is then terminated by addition of methanol. Following termination of the reaction, the assay tubes are centrifuged and the supernatant analyzed for the presence of cleaved compound fragment. Analysis of the supernatant can be performed by any number of well known techniques including, but not limited to, spectrofluorometric analysis, high pressure liquid chromatography or mass spectrometry. Compounds identified in these screening assays as potential anticancer prodrugs may require chemical modification for optimize their anti-tumor activity.

The following non-limiting examples are provided to further illustrate the claimed invention.

EXAMPLES

Example 1

Identification of CEs

A CE enzyme suitable for converting CPT-11 to the active form, SN-38 was identified by testing a variety of samples. This screening included enzymes from a series of sera, cell extracts and commercially available CEs using a rapid fluorometric assay. Certain of these enzymes show activity in metabolism of CPT-11.

Since partially purified CEs were commercially available, several of these were also tested for their ability to metabolize CPT-11. Both rabbit and pig liver CEs metabolized CPT-11 efficiently. The commercially available pig CE contained several proteins. However, the major bands were very similar in molecular weight and did not separate using SDS-PAGE. In contrast, the rabbit preparation consisted of only one major and one minor protein. Therefore, the rabbit proteins were chosen for further study.

The rabbit proteins were subjected to automated N-terminal amino acid sequencing. Both bands yielded protein sequences indicating that the peptides were not N-terminally blocked. The derived amino acid sequences were analyzed by computer searches using the Fasta and BLAST comparison programs. Band 1 (approximately 60 kDa) demonstrated significant homology with several CE sequences, including a rabbit CE, present in the GenBank and Swissprot databases (FIG. 1). However, the nucleic acid sequence encoding rabbit CE protein has not been disclosed. In addition, comparison of the amino acid sequence of the polypeptide encoded by the cDNA of the present invention with the published amino acid sequence for rabbit CE showed three mismatches. Further, the polypeptide encoded by the cDNA of the present invention contains an 8 amino acid insert and an 18 amino acid leader sequence at the N-terminus which the published sequence does not contain. Thus, the published amino acid sequence of a rabbit liver carboxylesterase protein (Swissprot Accession Number P12337; Korza, G. and J. Ozols. 1988. *J. Biol. Chem.* 263:3486–3495) is different from the polypeptide encoded by the cDNA of the present invention.

In addition to the rabbit CE, studies were performed to isolate human CE from sources other than liver, since the human liver CE has been shown to be an inefficient enzyme for metabolism of CPT-11. Biopsies of human intestine were obtained from the Cooperative Human Tissue Network (Birmingham, Ala.). The samples were ground under liquid nitrogen and the resulting powder sonicated in 50 mM Hepes, pH 7.4, on ice. CE activity and CPT-11 conversion were monitored by these extracts.

Example 2

Cloning of Rabbit Carboxylesterase

The cDNA encoding the rabbit CE protein of the present invention was isolated by synthesizing degenerate oligonucleotides from amino acid residues 1–5 (SEQ ID NO:6) and 518–524 (SEQ ID NO:10) of the published protein sequence of a rabbit liver CE (Korza, G. and J. Ozols. 1988. *J. Biol. Chem.* 263:3486–3495). The oligonucleotides constructed are shown in FIG. 2. To amplify the rabbit cDNA by PCR, cDNA was prepared from rabbit liver poly A+ MRNA and multiple samples were prepared that contained the combination of oligonucleotide primers. Following heating at 95° C. for five minutes, the polymerase was added at the annealing temperature and reactions cycled as follows: 94° C. 45 seconds, annealing temperature (46–58° C.) 1 minute, 72° C. 90 seconds. Typically, 25 cycles of amplification were performed. A single product was obtained from one set of reactions that upon DNA sequencing was shown to encode a novel rabbit CE.

Since this represented a partial CDNA, both 5' and 3' RACE were used to amplify the entire coding sequence. Unique primers of 27 and 28 nucleotides, corresponding to the 5' and 3' ends respectively, were designed from the partial DNA sequence. These oligonucleotides were used in combination with the AP1 primer to amplify sequences prepared from Marathon adapted rabbit liver cDNA. Touchdown PCR (Don, R. H. et al. 1991. *Nucleic Acids Res.* 19:4008) was performed as according to the Marathon cDNA amplification protocol. A single product of approximately 420 bp was generated by the 3' primer, however no product was observed with the 5' oligonucleotide. Standard PCR amplification protocols (94° C. 45 seconds, 60° C. 1 minute, 72° C. 1 minute, 30 cycles) resulted in a smear of DNA products with a minor band at approximately 280 bp. Attempts to increase the specificity of the reaction were unsuccessful. Therefore, DNA was isolated from the agarose gels and then ligated into pCRII-TOPO. DNA sequencing indicated the presence of the oligonucleotide RACE primers in both samples. The 3' RACE product extended 407 bp from the specific primer and encoded the terminal amino acids consistent with the published data (Korza, G. and J. Ozols. 1988. *J. Biol. Chem.* 263:3486–3495). In addition, a poly A tail was present and the original Marathon cDNA synthesis primer sequences could be identified. The 5' RACE product extended 247 bp from the CE specific primer and encoded the published amino acid sequence. An additional 18 residue hydrophobic leader sequence beginning with a methionine initiation codon was identified, consistent with the amino acids present at the N-termini of CEs derived from other species (FIG. 3). The entire transcript including both untranslated 5' and 3' sequences, as determined by the RACE experiments, was 1886 nt long, very similar to that indicated by the Northern analysis. This confirmed that the cDNA described in these experiments was full length.

To amplify a full length rabbit CE CDNA, oligonucleotide primers RabNTERM (GGCAGGAATTCTGCCATGTGGCTCTG; SEQ ID NO:23) and RabCTERM (CGGGAATTCACATTCACAGCTCAATGT; SEQ ID NO:24) were designed to create EcoRI sites 9 bp upstream of the ATG initiation codon and 8 bp downstream of the TGA termination codon. These were used to amplify rabbit liver cDNA using Pfu polymerase. The initial 5 cycles of amplification were performed as follows: 94° C., 45 seconds; 50° C., 1 minute; 72° C., 90 seconds with the annealing temperature raised to 56° C. for the subsequent 25 cycles. This allowed the formation of the EcoRI restriction sites at the termini of the cDNA. A product of approximately 1700 bp was obtained, ligated into pUC9 restricted with EcoRI and the entire DNA was sequenced.

Example 3

Expression of Rabbit CE in *Spodoptera frugiperda* Sf21

Cells ($4 \times 10^7$) were plated in the lower chamber of an Integra CL1000 flask (Integra Biosciences, Ijamsville, Md.)

in 45 mls of Insect Xpress media (Biowhittaker, Walkersville, Md.). To ensure adequate growth of the cells, 500 mls of complete Grace's media was added to the upper chamber of the flask. After incubation at 27° C. for 2 days, baculovirus were added to the cells in the lower chamber at a multiplicity of infection of 20. Media in the lower chamber was assayed every 24 hours for carboxylesterase (CE) activity and usually harvested after 120 hours. The secreted CE was concentrated by ultrafiltration to yield approximately 1 ml of sample containing approximately 30,000 micromoles/ml of enzyme activity.

Example 4

Amplification of Human Intestinal CB cDNA

The full length coding sequence of the human intestinal CE (GenBank Accession No. Y09616) was obtained by PCR using oligonucleotide primers HumICE3' (CGGTCTAGAGAGCTACAGCTCTGTGTGTCTG; SEQ ID NO:29) and HumICE5' (CGAGTCTAGAGAGCCGACCATGCGGCTGCAC; SEQ ID NO:30) that created XbaI restriction sites adjacent to the ATG initiation and TAG termination codons. The cDNA was amplified from human liver cDNA (Clontech, Palo Alto, Calif.) using Taq polymerase under the following conditions; denaturation at 94° C., 45 seconds, annealing at 50° C., 1 minute, and extension at 72° C., 2 minutes. Following 30 cycles of amplification, products were ligated into pCR-II TOPO and sequenced to verify their identity. One clone containing the bona fide sequence was ligated into pCIneo (pCIhiCE) for expression in mammalian cells. Plasmids containing the human liver CE (hCE1; PCIHUMCAR) and the rabbit liver CE (pCIRAB) have been previously described (Potter et al. 1998. *Cancer Res.* 52:2646–2651; Potter et al. 1998. *Cancer Res.* 58:3627–3632).

Example 5

Transfection of COS-7 Cells with Human Intestinal CE

COS-7 cells were transfected by electroporation as previously described (Potter et al. 1998 *Cancer Res* 52:2646–2651). Extracts were prepared by sonication of cell pellets in minimal volumes of 50 mM HEPES (pH 7.4) on ice 48 hours following transfection.

Esterase Assays

Esterase activity was determined in whole tissue sonicates using a spectrophotometric assay with o-nitrophenol acetate as a substrate (Potter et al. 1998 *Cancer Res.* 52:2646–2651; Beaufay et al. 1974 *J. Cell Biol.* 61:188–200). Protein concentrations were calculated using BioRad protein assay reagent (Hercules, Calif.) with bovine serum albumin as a standard. Enzyme activities were calculated as $\mu$moles of o-nitrophenol produced per minute per mg of total protein.

Transfection of Mammalian Cells

COS-7 cells ($10^7$) were electroporated with 20 $\mu$g of plasmid DNA in a volume of 200 $\mu$l of phosphate buffered saline using a Biorad electroporator and a capacitance extender (Biorad, Hercules, Calif.). Optimized conditions for electroporation were achieved using 260 V and 960 $\mu$F. Following transfection, cells were plated into 75 cm² flasks in fresh media and harvested by trypsinization after 48 hours.

CPT-11 Conversion Assays

Appropriate amounts of extracts were incubated with 5 $\mu$M of CPT-11 in a final volume of 200 $\mu$l of 50 mM HEPES pH 7.4 at 37° C. for 24 hours. Reactions were terminated by addition of 200 $\mu$l cold acid-methanol and centrifuged for 15 minutes at 16000 g. The conversion of CPT-11 to SN-38 was monitored by high performance liquid chromatography (HPLC) in 20 $\mu$l sample volumes.

Example 6

In vitro Biological Activity of Rabbit CE

The in vitro activity of rabbit liver CE was examined in tumor cell lines. The growth inhibition of CPT-11 was compared in cells with and without active rabbit CE. The cells used were Rh30 cells ($10^7$) that had been electroporated with 20 $\mu$g of IRES plasmid DNA or plasmid containing CE cDNA in a volume of 200 $\mu$l of phosphate buffered saline. Optimized conditions for electroporation were achieved using 180 V and 960 $\mu$F. The cells were plated into 75 cm² flasks in fresh media and 500 $\mu$g G418/ml added 48 hours following transfection to select for cells expressing the neo gene and the CE. Cells were grown for a minimum of 10 days before use in growth inhibition experiments.

In the first assay, CPT-11 was pre-incubated with rabbit liver CE to produce SN-38 prior to exposure of the cells to drug. Specifically, 0.5 to 5 units of CE were incubated with 1 $\mu$M CPT-11 at 37° C. in DMEM medium for 2 hours. Each reaction mixture was then filter-sterilized and Rh30 cells were exposed to drug for one hour, at which time the medium was replaced with drug-free medium containing serum. Enzyme that had been inactivated by boiling for five minutes prior to incubation with drug or CPT-11 to which no enzyme had been added were used as negative controls. Cells were allowed to grow for 3 cell doubling times and cell numbers were determined.

In the second type of growth inhibition assay, Rh30 cells that had been transfected with either pIRES parent plasmid DNA or the plasmid containing the rabbit CE cDNA were exposed to different concentrations of CPT-11. Drug was added to tissue culture medium of each of the stably transfected cell lines for two hours, after which time the medium was replaced with drug-free medium. Cells were then allowed to grow for 3 cell doublings as before. Results were expressed as the concentration of drug required to reduce cell growth to 50% of control cells, or $IC_{50}$.

Results showed that extracts of the transfected cells contained greater than 60-fold more CE activity than controls as determined by the conversion of o-nitrophenyl acetate to o-nitrophenol. Further, the Rh30pIRES cells transfected with rabbit CE were greater than 8-fold more sensitive to CPT-11 than controls, as shown by a decrease in the $IC_{50}$ values. Therefore, Rh30 cells stably transfected with rabbit CE were more sensitive to growth inhibition by CPT-11 than cells that did not contain the cDNA for rabbit CE.

Example 7

In vitro Biological Activity of Human Intestinal CE

CE activity was determined by the spectrophotometric method described above for rabbit CE samples using o-NPA as a substrate. In another assay, activation of CPT-11 was determined by incubating samples of hiCE with either 5 $\mu$M or 25 $\mu$M CPT-11 in a total volume of 200 $\mu$l of 50 mM Hepes pH 7.4 at 37° C. for up to 20 hours. Reactions were terminated by the addition of an equal volume of cold acidified methanol, followed by centrifugation at 100,000×g for 30 minutes. The levels of SN-38 produced in the reaction were quantitated by HPLC.

Growth inhibition assays were performed with COS-7 cells as previously described (Potter et al. 1998 *Cancer Res.*

52:2646–2651; Danks et al. 1998 *Cancer Res.* 52:2646–2651, 1998). Forty-eight hours after transfection, 5×10⁴ cells were plated into 1.5 cm diameter dishes and allowed to attach overnight. CPT-11 diluted in fresh medium was applied for two hours and the cells allowed to grow for three days, equivalent to three cell doublings. Cell number was determined by counting using a Coulter Multisyser II (Coulter Electronics, Luton, England) and growth inhibition curves were plotted using Prism software (GraphPad Software Inc., San Diego, Calif.). $IC_{50}$ values (the concentration of drug required to reduce cell growth by 50%) were calculated from these curve fits.

Example 8

Rabbit CE Activates APC, a Novel Prodrug

In addition to efficiently converting CPT-11 to the active compound SN-38, experiments were also performed demonstrating the ability of rabbit liver CE to convert the inactive metabolic end product APC to SN-38. No known human enzyme activates APC. FIG. 6 shows the kinetics of conversion of APC to SN-38 by 50 units of rabbit liver CE in an in vitro reaction. FIG. 7 shows that U-373 glioma cells that express the rabbit liver CE, but not human alveolar macrophage carboxylesterase which is 85% homologous to the rabbit enzyme, are sensitized to the growth inhibitory effects of APC. Thus, the combination of APC and sensitization of selected tumor cells with rabbit liver CE as described above can be used to produce a tumor-specific cell death while greatly minimizing the toxic side effects associated with administration of chemotherapy.

Example 9

Use of Rabbit CE in an In vivo Model for MRD

A xenograft model for MRD has been developed to demonstrate the effectiveness of the combination of rabbit CE and prodrug in the prevention of MRD. In this model, treatment of immune-deprived mice, i.e., SCID mice, bearing human NB-1691 xenografts with 10 mg/kg CPT-11 daily for 5 days on two consecutive weeks results in complete regression of the tumor. However, within 4–6 weeks, tumors are palpable in the exact position where the original xenograft was implanted. Since these tumors arise from cells that survived the initial cycle of chemotherapy, this model therefore mimics results seen in patients following surgical resection of the primary tumor and subsequent regrowth at the same site.

Experiments were performed in this model to compare the responses of mice bearing human Rh30 and Rh30pIRES$_{rabbit}$ xenografts. Rh30 rhabdosarcoma xenografts were transfected with pIRESneo plasmid containing the cDNA for rabbit liver CE and selected with G418. Expression of CE was confirmed by biochemical assay using the CE substrate o-NPA and maintained for at least 12 weeks. Two groups of SCID mice were then injected with the transfected Rh30pIRES$_{rabbit}$ cells subcutaneously into the flanks. A third group of control mice was injected in identical fashion with Rh30 cells not transfected with the plasmid. When the tumors reached a size of approximately 1 cm³, 2.5 mg CPT-11/kg/day was administered five days each week for two weeks (one cycle of therapy), repeated every 21 days for a total of three cycles (over 8 weeks) to one group of mice injected with the transfected Rh30pIRES$_{rabbit}$ cells and the third group of control mice.

The tumors expressing rabbit CE regressed completely and did not regrow during the 12 weeks of the study (FIG. 9B). In contrast, tumors not expressing the CE regressed only transiently, regrowing within one week after CPT-11 treatment had stopped (FIG. 9C).

Similar studies were performed employing U373 glioblastoma cells transfected with the pIRESneo plasmid or with pIRESneo containing the cDNA for rabbit liver CE and selected with G418. Expression of CE in the tumor cells was confirmed by biochemical assay using the substrate o-NPA. Cells were injected subcutaneously into the flanks of the SCID mice. When tumors reached approximately 1 cm³ in size, CPT-11 was administered daily for five days each week as described above, for three cycles, at a dose of 7.5 mg/kg/day.

The U373 cells that expressed rabbit CE were also more sensitive to CPT-11. Xenografts established from cells transfected with the plasmid encoding rabbit CE regressed completely while xenografts from cells transfected with the control plasmid showed stable disease with no significant regression. These data in two different human tumor xenografts demonstrate the in vivo efficacy of rabbit CE to sensitize tumor cells to CPT-11.

Similar experiments can be performed to assess the in vivo efficacy of hiCE in preventing MRD. In these experiments, adenovirus expressing hiCE under control of a tumor-specific promoter is administered subcutaneously at the site of xenograft implantation in this model during the 4 to 6 week period when tumors are not present, followed by treatment with low doses of CPT-11. Typically, since tumor regression is complete 3 weeks after commencing treatment with CPT-11, adenovirus/drug administration begins at week 4. In initial experiments, adenovirus is administered on Monday, Wednesday, Friday and CPT-11 is given daily on Tuesday through Saturday for two cycles. This permits determination of the most tolerated, effective schedule and dosage of adenovirus and CPT-11 administration to produce the longest delay of recurrent disease. These results are used to determine correct dosage for treatment of human MRD. The starting point for the animal experiments is injection of $10^5$ to $10^8$ pfu of adenovirus containing the hiCE of the present invention.

Example 10

Use of a CE/Prodrug Combination to Purge Bone Marrow of Tumor Cells

Intravenous injection of human neuroblastoma NB-1691 tumor cells into immune-deprived mice results in the development of widespread metastatic disease with death occurring on days 36–38. Since both synaptophysin and tyrosine hydroxylase expression are specific for neuroblastoma cells, RT/PCR analysis of these mRNAs can detect tumor cells present in mixed populations of cells. Circulating neuroblastoma cells can be detected in the peripheral blood of these animals 36 days after injection with NB-1691. Studies will then determine whether the bone marrow of these same animals contains neuroblastoma cells. The success of ex vivo purging of bone marrow with the rabbit liver CE/CPT-11 combination or the human intestinal CE/CPT-11 combination is demonstrated by transplanting purged bone marrow into lethally irradiated mice. If mice remain disease free for extended periods of time, this indicates that the adenoviral CE/prodrug purging therapy kills neuroblastoma cells in the donor marrow.

Example 11

Treatment of Minimal Residual Disease (MRD) in Humans

The rabbit CE or human intestinal CE in combination with CPT-11 or other prodrugs activated by this enzyme is used to purge bone marrow of residual tumor cells prior to autologous bone marrow transplants to prevent recurrence of local MRD following removal of bulk tumor by surgery or chemotherapy. Following debulking of the primary tumor, adenovirus containing the rabbit liver CE or human intestinal CE under the control of a tumor-responsive promoter is applied to the tumor margins at either the time of surgery, by stereotaxic injection, or by implantation of a time-release polymer or other material. Anti-tumor effect of single application at time of surgery is compared with the effect produced by repetitive or time-release use of adenoviral constructs. Adenovirus dose ranges from $10^6$ to $10^{10}$ plaque-forming units as has been reported to be effective for intratumoral injection of adenovirus (Heise, C. et al. 1977. Nature Med. 3:639–645). CPT-11 is administered over the next one to six weeks to elicit tumor selective cell kill. Doses and schedules of CPT-11 are determined in clinical trials of CPT-11 by itself and in human xenograft model systems to produce maximal tumor effect.

Example 12

Purging Bone Marrow of Tumor Cells in Humans

Tumor cells that contaminate bone marrow used for autologous transplant contribute to relapse of disease. Therefore, the rabbit liver CE or the human intestinal CE is used in combination with a suitable prodrug to eradicate tumor cells in marrow samples to be used for transplant. This approach maintains the viability of hematopoietic cells required for reconstitution. Bone marrow samples are transduced ex vivo with adenovirus containing the rabbit liver CE cDNA or the human intestinal CE cDNA, using a multiplicity of infection (moi) that will infect 100% of the tumor cells. Typically, a moi of 0.5 to 10 is adequate for tumor cells, while a moi of 100 to 1,000 is required to transduce a majority of hematopoietic progenitor cells. Two days following adenoviral transduction, cells are exposed for two hours to a range of CPT-11 concentrations, usually varying from 50 nM to 100 $\mu$M. Two days after exposure to drug, the marrow sample is harvested and stored for reinfusion into the patient and reconstitution of a tumor-free marrow.

What is claimed is:

1. A method for sensitizing tumor cells to a chemotherapeutic prodrug APC or CPT-11 in vitro comprising transfecting selected tumor cells with a composition comprising an isolated polynucleotide encoding a carboxylesterase wherein said carboxylesterase is operably linked to a promoter that directs expression of said carboxylesterase in said tumor cells, and wherein expression of the carboxylesterase renders the tumor cells more sensitive to the cytotoxic effect of said chemotherapeutic prodrug APC or CPT-11.

2. A method of inhibiting tumor cell growth in vitro comprising:

(A) sensitizing tumor cells in accordance with the method of claim 1; and
(B) contacting said sensitized tumor cells with said chemotherapeutic prodrug CPT-11 or APC so that tumor cell growth is inhibited.

3. The method according to claim 1 wherein the carboxylesterase is selected from the group consisting of rabbit carboxylesterase and human intestinal carboxylesterase.

4. The method according to claim 1 wherein the carboxylesterase is delivered by an adenoviral vector.

* * * * *